(12) United States Patent
Comenge Farré

(10) Patent No.: US 12,364,772 B2
(45) Date of Patent: Jul. 22, 2025

(54) CONJUGATES COMPRISING NANOPARTICLES COATED WITH PLATINUM DERIVATIVES THROUGH SULFONYL OR PHOSPHONYL-CONTAINING LINKERS

(71) Applicant: NANONICA S.A., Lugano (CH)

(72) Inventor: Joan Comenge Farré, Barcelona (ES)

(73) Assignee: NANONICA S.A., Lugano (CH)

( * ) Notice: Subject to any disclaimer, the term of this patent is extended or adjusted under 35 U.S.C. 154(b) by 1049 days.

(21) Appl. No.: 17/421,000

(22) PCT Filed: Jan. 8, 2020

(86) PCT No.: PCT/EP2020/050294
§ 371 (c)(1),
(2) Date: Jul. 6, 2021

(87) PCT Pub. No.: WO2020/144222
PCT Pub. Date: Jul. 16, 2020

(65) Prior Publication Data
US 2022/0080054 A1    Mar. 17, 2022

(30) Foreign Application Priority Data
Jan. 8, 2019 (EP) .................... 19382009

(51) Int. Cl.
*A61K 47/69* (2017.01)
*A61K 33/243* (2019.01)

(52) U.S. Cl.
CPC ........ *A61K 47/6929* (2017.08); *A61K 33/243* (2019.01)

(58) Field of Classification Search
CPC .................................. A61K 47/6929
See application file for complete search history.

(56) References Cited

U.S. PATENT DOCUMENTS
2006/0099146 A1    5/2006 Chow et al.

FOREIGN PATENT DOCUMENTS
WO    WO 2010/069941 A1    6/2010

OTHER PUBLICATIONS

International Search Report and Written Opinion mailed Apr. 9, 2020 for Application No. PCT/EP2020/050294, 11 pages.
(Continued)

*Primary Examiner* — Benjamin J Packard
(74) *Attorney, Agent, or Firm* — Squire Patton Boggs (US) LLP

(57) ABSTRACT

The present invention relates to conjugates having colloidal stability in a medium which comprises a nanoparticle NP, a plurality of linkers of formula (II) comprising a sulfonyl moiety or a phosphonyl moiety as defined herein, and a plurality of groups A attached to the linkers, wherein: NP is a gold, silver or platinum nanoparticle; with the condition that an amount equal to or higher than 50% of the linkers of formula (II) are in ionic form when the conjugate is in an aqueous medium. It also relates to a process for the preparation of these conjugates and to pharmaceutical compositions containing them. The conjugates of the invention are used for the treatment of cancer.

19 Claims, 5 Drawing Sheets

(II)

(56) References Cited

OTHER PUBLICATIONS

Bastús, et al: "Kinetically controlled seeded growth synthesis of citrate-stabilized gold nanoparticles of up to 200 nm: Size focusing versus Ostwald ripening", Langmuir; Jul. 5, 2011; vol. 27(17), pp. 11098-11105.
Fiurasek, et al: "Phosphonic and sulfonic acid-functoinalized gold nanoparticles: A solid state NMR study", Langmuir; Feb. 1, 2007 (e-pub Jan. 13, 2007); vol. 23(5), pp. 2857-2866.
Tan, et al: "Surface modification of cisplatin-complexed gold nanoparticles and its influence on colloidal stability, drug loading, and drug release", Langmuir 2018 (online Nov. 15, 2017); vol. 34(1), pp. 154-163.
Zhang, et al: "Facile controlled preparation of phosphonic acid-functionalized gold nanoparticles" Journal of Colloid and Interface Science; Nov. 15, 2010; vol. 351(2), pp. 421-426.

CONJUGATES COMPRISING NANOPARTICLES COATED WITH PLATINUM DERIVATIVES THROUGH SULFONYL OR PHOSPHONYL-CONTAINING LINKERS

This application is a 35 U.S.C. § 371 national phase application of PCT/EP2020/050294 filed on Jan. 8, 2020, which claims the benefit of European Patent Application 19382009.9 filed on Jan. 8, 2019; the entire contents of both applications are incorporated by reference in their entireties.

TECHNICAL FIELD

The present invention relates to conjugates which comprise nanoparticles functionalized with platinum compounds, where the chemotherapeutic agent is at least partially attached to the nanoparticle through a specific linker having a sulfonyl or phosphonyl end group. The conjugates of the invention show increased drug release, and improved stability and efficacy against tumor cells. The invention also relates to a process for the preparation of these conjugates and to pharmaceutical compositions containing them, as well as to their use in the treatment of cancer.

BACKGROUND ART

Platinum compounds play an important role in cancer chemotherapy. Cisplatin, the first generation of platinum based chemotherapy drug, is one of the most common anticancer agents and has a wide spectrum of anticancer activity. However, drawbacks such as the poor selectivity between malignant and normal cells, leading to severe toxic effects (such as nephrotoxicity, neurotoxicity and ototoxicity) and the presence of intrinsic or acquired resistance, so that the doses must be increased, importantly limit its efficacy. Moreover, cisplatin has additional drawbacks, such as low solubility in aqueous solutions and side effects such as nausea and vomiting.

Although extensive efforts were devoted to overcoming these major issues by developing new generations of platinum derivatives that are less toxic and more active than cisplatin and/or do not display cross-resistance, the improvements are still rather small. Thus, second generation platinum-based drugs, such as carboplatin or oxaliplatin, have lower renal and gastrointestinal toxicities but bone marrow toxicity caused by carboplatin and neurotoxicity of oxaliplatin are limitant. Their anticancer spectrum and efficacy are different than cisplatin.

Drug delivery systems in which carriers incorporate the drug either through chemical bonding or passive adsorption may deliver the drug to specific cells and avoid elimination by the immune system. Ideally, such delivery systems extravasate the tumor vasculature and accumulate within the tumor environment. A particle delivery system capable to release a cancer drug solely within the tumor may also reduce the accumulation of the drug in healthy tissues.

There are several drug delivery systems described in literature that are based on nanomaterials. In some cases, the drug is adsorbed on the nanomaterial or encapsulated into nanocapsules. In other cases, it is covalently attached to the surface of the nanomaterial.

In this context, WO 2010/069941 discloses platinum derivatives conjugated to gold nanoparticles via sulfur-containing linkers having carboxyl end groups, such as e.g. 11-mercaptoundecanoic acid (MUA), for the treatment of cancer.

The research of new drug delivery systems in cancer is still an emerging field and there is a need for further exploring delivery systems which increase the relative efficacy and safety of a cancer therapy and reduce tumor resistance.

SUMMARY OF INVENTION

The inventors have found that when the platinum-containing conjugates disclosed in WO 2010/069941 are modified such that the carboxyl end groups of the linkers are replaced at least partially by sulfonyl or phosphonyl end groups, the resultant conjugates show an increased release of the attached platinum compounds at a higher release rate.

Besides, as illustrated in the examples below, the modification of the linker's terminal carboxylic acid by an acid moiety of an heteroatom such as P or S not only has an impact on the release profile, but it also unexpectedly improves both the stability of the conjugates in physiologic conditions, and their efficacy against tumor cells, which might help to reduce tumor resistance.

Any effects on efficacy of the conjugates in vivo cannot be predicted a priori from a given release profile because of the risk-benefit balance. Thus, while it could be expected that a higher release at a higher rate could be advantageous for obtaining a faster antitumoral effect, this could also lead to an increased unspecific release and therefore a potential toxicity due to high systemic accumulation of the free chemotherapeutic drug.

Additionally, it is hardly foreseeable how a change in the physico-chemical properties of the conjugate, in particular a change in the end groups of the linkers, (e.g., surface charge and/or density of the ligand layer) may affect the efficacy against tumoral cells taking into account that there are many actors that play a role in vivo such as e.g. cell uptake, interactions with the immune system, as well as tumor penetration of the conjugate, which ultimately determines more or less accumulation by Enhanced Permeability and Retention (EPR) effect in the tumors.

In addition, the conjugates of the invention are highly soluble in comparison with the currently used free platinum compounds, whose solubility is low.

Therefore, a first aspect of the present invention refers to a conjugate having colloidal stability in a medium which comprises a nanoparticle NP, a plurality of linkers L attached to the nanoparticle, and a plurality of groups A attached to the linkers, wherein:
NP is a gold, silver or platinum nanoparticle;
the linkers L comprise linkers of formula (II):

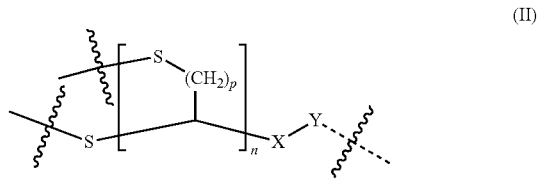

wherein:
n represents 0 or 1; wherein:
when n is 0, the linker of formula (II) is attached to the nanoparticle NP through one sulfur atom; and
when n is 1, the linker of formula (II) is attached to the nanoparticle NP through two sulfur atoms;
p represents a value selected from 1 to 3; and X represents a $(C_2-C_{20})$hydrocarbon chain, or a $(C_2-C_{20})$hydrocarbon chains wherein at least one carbon atom is replaced by a carbonyl group or a heteroatom selected from the group consisting of O and N; and wherein these $(C_2-C_{20})$hydrocarbon chains are optionally substituted with one or more substituents selected from the group consisting of halogen, OH, $CONH_2$, $CO_2(C_1-C_6)$alkyl and —CHO;

---- is either absent or alternatively represents a single bond; wherein:

when ---- is absent, Y is either a sulfonyl moiety of formula (i), or alternatively a phosphonyl moiety of formula (ii):

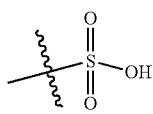

(i)

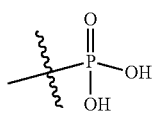

(ii)

and when ---- is a single bond, Y is either a sulfonyl moiety of formula (i'), or alternatively a phosphonyl moiety of formula (ii'), which is attached to A by the oxygen atom:

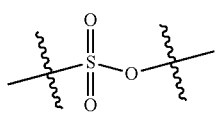

(i')

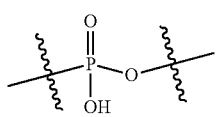

(ii')

the groups A are platinum (II) biradicals independently selected from the group consisting of formula (IV), formula (V), formula (VI), and a pharmaceutically acceptable salt of any of them:

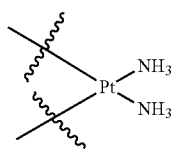

(IV)

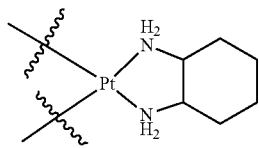

(V)

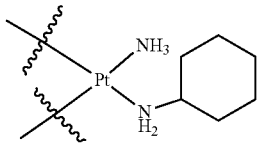

(VI)

wherein the platinum (II) biradical is attached to two independent linker molecules of formula (II) wherein ---- is a single bond, and Y is either a sulfonyl moiety of formula (i'), or alternatively a phosphonyl moiety of formula (ii'), through the oxygen atom of the moiety of formula (i') or (ii');

with the condition that an amount equal to or higher than 50% of the linkers L of the conjugate are in ionic form when the conjugate is in an aqueous medium.

This aspect may also be formulated as a conjugate having colloidal stability in a medium which comprises a nanoparticle NP, and a plurality of linkers L attached to the nanoparticle, wherein an amount equal to or lower than 50% of the linkers L are also attached to groups A; and wherein the nanoparticle NP, the linkers L, the groups A are as previously defined.

Particularly, in the first aspect of the invention, an amount equal to or higher than 55% of the linkers L are linkers of formula (II). Thus, a second aspect of the invention relates to a conjugate having colloidal stability in a medium which comprises a nanoparticle NP, a plurality of linkers L which are attached to the nanoparticle, and a plurality of groups A attached to the linkers; wherein an amount equal to or higher than 55% of the linkers L are linkers of formula (II); wherein the nanoparticle NP, the linkers of formula (II), and the groups A are as previously defined; and with the condition that an amount equal to or higher than 50% of the linkers L of the conjugate are in ionic form when the conjugate is in an aqueous medium.

This second aspect may also be formulated as a conjugate having colloidal stability in a medium which comprises a nanoparticle NP, and a plurality of linkers L attached to the nanoparticle, wherein:
i) an amount equal to or lower than 50% of the linkers L are attached to groups A,
ii) an amount equal to or higher than 55% of the linkers L are linkers of formula (II);
and wherein the nanoparticle NP, the linkers of formula (II), and the groups A are as previously defined.

A third aspect relates to conjugate having colloidal stability in a medium which comprises a nanoparticle NP, a plurality of linkers of formula (II) attached to the nanoparticle,

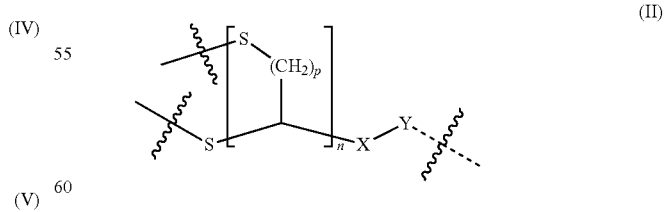

(II)

and a plurality of groups A attached to the linkers, wherein:
NP is a gold, silver or platinum nanoparticle;
n represents 0 or 1; wherein:
when n is 0, the linker of formula (II) is attached to the nanoparticle NP through one sulfur atom; and when n is 1, the linker of formula (II) is attached to the nanoparticle NP through two sulfur atoms;

p represents a value selected from 1 to 3; and

X represents a $(C_2-C_{20})$hydrocarbon chain, or a $(C_2-C_{20})$ hydrocarbon chain wherein at least one carbon atom is replaced by a carbonyl group or a heteroatom selected from the group consisting of O and N; and wherein these $(C_2-C_{20})$hydrocarbon chains are optionally substituted with one or more substituents selected from the group consisting of halogen, OH, $CONH_2$, $CO_2(C_1-C_6)$ alkyl and —CHO;

---- is either absent or alternatively represents a single bond; wherein:

when ---- is absent, Y is either a sulfonyl moiety of formula (i), or alternatively a phosphonyl moiety of formula (ii):

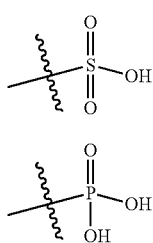

(i)

(ii)

and when ---- is a single bond, Y is either a sulfonyl moiety of formula (i'), or alternatively a phosphonyl moiety of formula (ii'), which is attached to A by the oxygen atom:

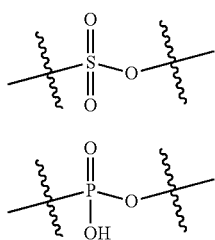

(i')

(ii')

the groups A are platinum (II) biradicals independently selected from the group consisting of formula (IV), formula (V), formula (VI), and a pharmaceutically acceptable salt of any of them:

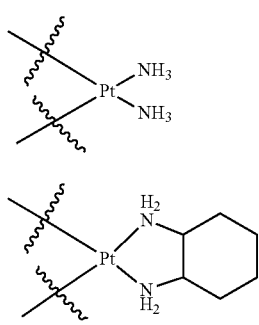

(IV)

(V)

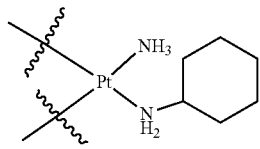

(VI)

wherein the platinum (II) biradical is attached to two independent linker molecules of formula (II) wherein ---- is a single bond, and Y is either a sulfonyl moiety of formula (i'), or alternatively a phosphonyl moiety of formula (ii'), through the oxygen atom of the moiety of formula (i') or (ii');

with the condition that an amount equal to or higher than 50% of the linkers of formula (II) are in ionic form when the conjugate is in an aqueous medium.

This third aspect may also be formulated as a conjugate having colloidal stability in a medium which comprises a nanoparticle NP, and a plurality of linkers of formula (II) attached to the nanoparticle; wherein an amount equal to or lower than 50% of the linkers of formula (II) are attached to groups A; and wherein the nanoparticle NP, the linkers of formula (II), and the groups A are as previously defined.

The stable colloidal conjugates of the invention can be conveniently prepared by an appropriate conjugation method. Therefore, another aspect of the invention refers to a process for the preparation of a conjugate as defined above, comprising the following steps:

a) reacting a gold, silver or platinum nanoparticle NP with an excess of a compound selected from the group consisting of formula (IIa), formula (IIb), and a salt either of the compound of formula (IIa) or of the compound of formula (IIb),

(IIa)

(IIb)

wherein X, and p have the same meaning as defined above, and Y is a sulfonyl moiety of formula (i') or a phosphonyl moiety of formula (ii') as defined above; in an aqueous solution to give rise to an intermediate conjugate; wherein:

when a compound of formula (IIa) or a salt thereof is used, an intermediate conjugate is obtained wherein in the linker of formula (II), n is 0; and when a compound of formula (IIb) or a salt thereof is used, an intermediate conjugate is obtained wherein in the linker of formula (II), n is 1;

b) reacting the intermediate conjugate obtained in step a) with an appropriate amount of a platinum (II) compound selected from the group consisting of formula (IVa), formula (Va), formula (VIa), and a salt of any of the formulas (IVa), (Va) or (VIa):

(IVa)

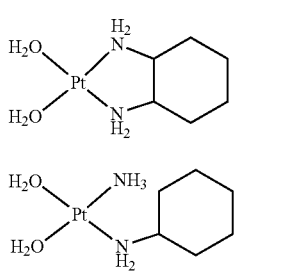

in an aqueous solution in the presence of a base, to obtain the desired conjugate.

The conjugates of the present invention may be administered to mammals, including humans, suffering from a cancer. Thus, another aspect of the present invention relates to pharmaceutical compositions comprising the conjugates as defined above together with one or more pharmaceutically acceptable excipients or carriers.

A further aspect of the invention relates to a conjugate as defined above for use in cancer. Therefore, this aspect relates to the use of the conjugates as defined above for the manufacture of a medicament for the treatment of cancer. Alternatively, this aspect may also be formulated as a method for the treatment of cancer in a mammal, including a human, the method comprising administering to said mammal an effective amount of the previously defined conjugates as defined above together with one or more pharmaceutically acceptable excipients.

DETAILED DESCRIPTION OF THE INVENTION

Figure 1:
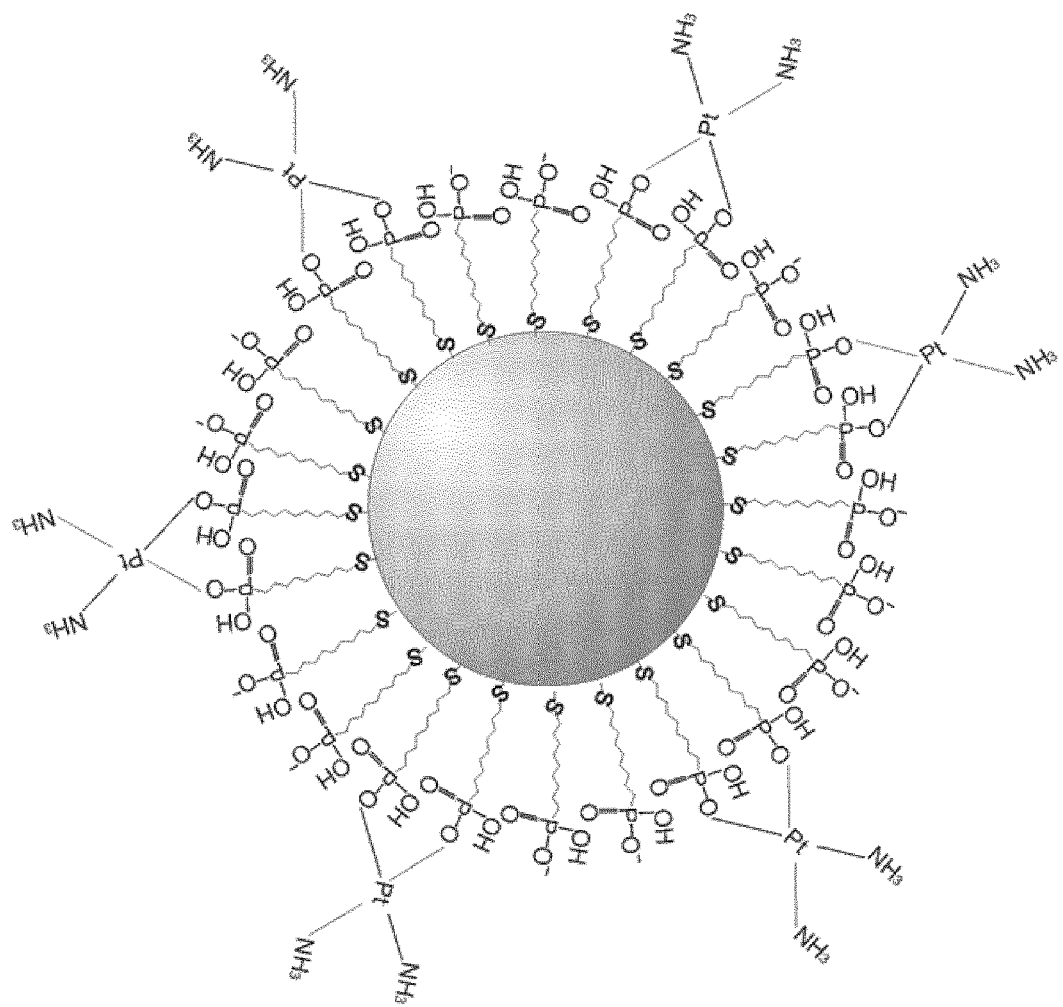
FIG. 1 shows a schematic view of a conjugate according to the invention, in particular a conjugate of formula (I) NP-L-A, wherein NP is a gold nanosphere; L corresponds to linker containing a phosphonyl moiety; and A is a platinum (II) biradical obtained from cisplatin.

All terms as used herein in this application, unless otherwise stated, shall be understood in their ordinary meaning as known in the art. Other more specific definitions for certain terms as used in the present application are as set forth below and are intended to apply throughout the description and claims.

The term "about" or "around" as used herein refers to a range of values±10% of a specified value. For example, the expression "about 10" or "around 10" includes±10% of 10, i.e. from 9 to 11.

As mentioned above, a first aspect of the present invention relates to a conjugate having colloidal stability in a medium which comprises a nanoparticle NP, a plurality of linkers L attached to the nanoparticle, and a plurality of groups A attached to the linkers.

For the purposes of the invention, "linkers L" refer to all the linkers present in the nanoparticle which may be of one type (i.e. only linkers of formula (II), which can be the same or different) or, alternatively, of different types (e.g. a mixture of linkers of formula (II) and linkers of formula (III)).

As used herein, the term "plurality" relates to a number greater than one, and is equivalent to the expressions "two or more" or "at least 2".

When the conjugates of the invention are defined as comprising a nanoparticle NP, a plurality of linkers L attached to the nanoparticle, and a plurality of groups A attached to the linkers, the term "plurality of linkers" and the term "plurality of groups A" do not have the same meaning, i.e. the number of linkers is not the same as the number of groups A as derived from the condition that an amount equal to or higher than 50% of the linkers L (i.e. all the linkers present in the conjugate) are in ionic form when the conjugate is in an aqueous medium. This condition can also be formulated such that an amount equal to or lower than 50% of the linkers L of the conjugate are attached to groups A. As explained below, for a conjugate to have colloidal stability it is needed that at least some of the linkers remain deprotonated in vivo and are not attached to groups A.

According to the invention, the term "conjugate" refers to a metallic nanoparticle (herein also referred to as NP) which is attached to a plurality of platinum compounds through linkers, wherein at least part of the linkers, particularly equal to or higher than 55% of the linkers, have a sulfonyl or phosphonyl end group. Using a simplified nomenclature, the conjugate of the invention is also referred herein to as NP-L-A. However, as described herein, this simplified nomenclature intends to describe a conjugate wherein not all the linkers L of the conjugate (being particularly 55% or more of the linkers L linkers of formula (II) having a sulfonyl or phosphonyl end group) are conjugated to platinum A groups. Particularly, an amount equal to or lower than 50% of the linkers of the conjugate are attached to groups A.

More particularly, the nanoparticle is attached to the plurality of linkers L through a pseudo-covalent bonds, like the one occurring between S and Au (about 45 kcal/mol), and part of the linkers are attached to the platinum compounds through a coordination bond between O and Pt. The coordination bond is not sensitive to weak variations of the pH. A significant release of the platinum drug is only obtained at pH below 5-6. Thus, while the conjugate is stable in serum, it releases its drug load when the pH is lowered, as it occurs in the endolysosome of a tumoral cell.

In the conjugates of the invention, the linkers and/or the platinum (II) biradicals may have chiral centres that can give rise to various stereoisomers. As used herein, the term "stereoisomer" refers to all isomers of individual linkers that differ only in the orientation of their atoms in space. The term stereoisomer includes mirror image isomers (enantiomers), mixtures of mirror image isomers (racemates, racemic mixtures), geometric (cis/trans or syn/anti or E/Z) isomers, and isomers of compounds with more than one chiral center that are not mirror images of one another (diastereoisomers). The present invention encompasses each of these stereoisomers and also mixtures thereof. Diastereoisomers and enantiomers can be separated by conventional techniques such as chromatography or fractional crystallization. Optical isomers can be resolved by conventional techniques of optical resolution to give optically pure isomers. This resolution can be carried out on any chiral synthetic intermediates or on compounds of the invention. Optically pure isomers can also be individually obtained using enantiospecific synthesis.

The conjugates of the invention comprise nanoparticles made of gold, silver or platinum. These metals show high affinity towards sulfur groups (including both thiol SH groups and disulfide S—S groups), such as the ones present in a compound of formula (IIa) or formula (IIb)

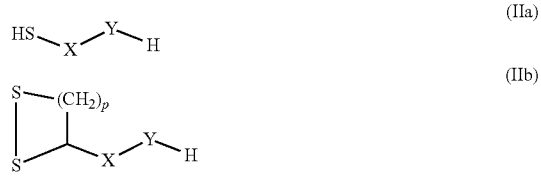

wherein X, and p have the meanings previously described, and Y is a sulfonyl moiety of formula (i') or a phosphonyl moiety of formula (ii') as defined above.

Thus, a free thiol group (SH) or a disulfide group (S—S) have a high tendency to spontaneously react with the metallic nanoparticle to form a pseudo-covalent bond metal-S. The strong binding between the linker and the nanoparticle is needed to avoid desorption of the linker molecule.

In addition, the inorganic nanoparticle is a good antenna for electromagnetic fields including for example gamma ray, X-ray, Near Infrared (NIR) or UV-Vis and microwaves).

In one embodiment, optionally in combination with one or more features of the various embodiments described above or below, gold nanoparticles (herein also referred to as AuNPs) are used. AuNPs have a strong surface plasmon enhanced absorption and scattering making them ideal as imaging labels and contrast agents. They are not susceptible to photobleaching, biocompatible and noncytotoxic. Moreover, they can be heated when they absorb light at their resonant frequency allowing photothermal therapy of cancer or they can enhance the efficacy of radiotherapy by the generation of Auger electrons after exposure of gold to x-rays.

For the purposes of the invention, the term "nanoparticles" refers to particles of nanometric size which may have different shapes and sizes. As regards the shape of the nanoparticles described herein, spheres and polyhedra comprising flat faces and straight edges are comprised within the scope of the invention. Examples of such polyhedra include, without limitation, cubes, prisms and rods. The polyhedra have the advantage that they can be near infrared (NIR)-sensitive and therefore the nanoparticles may be locally heated. In a preferred embodiment, the nanoparticles are spheres. In a preferred embodiment, the nanoparticles are gold nanospheres.

The size of the nanoparticle must be such that allows prolonged plasma life, i.e. the conjugate remains in the systemic circulation until it encounters hyperpermeable tumor capillaries.

In the case of nanospheres, the diameter is comprised in the range from 3 to 100 nm, preferably in the range from 4 to 20 nm.

In the case of nanocubes and nanoprisms, the size is defined in terms of the sphere, inscribed inside the nanocube or the nanoprism, which has the maximum diameter possible. In both cases, the diameter of said sphere is comprised in the range from 3 to 100 nm, preferably in the range from 4 to 20 nm.

Further, in the case of rods, the size is 100 nm length and 15 nm width, preferably 45 nm length×15 nm width.

The above-mentioned size values results in conjugates which are large enough to avoid the kidney, and small enough to minimize interactions with the reticuloendothelial system, part of the immune system, consisting of the phagocytic cells located in reticular connective tissue, primarily monocytes and macrophages. Moreover, this size of the conjugates of the invention (above that of essential small molecules as amino acids or small peptides) promotes endocytosis.

In one embodiment, optionally in combination with one or more features of the various embodiments described above or below, the nanoparticles are nanospheres of the invention have a diameter equal to or less than 20 nm, more particularly, from 4 to 20 nm, from 10 to 20 nm, and even more particularly about 14 nm. In a more particular embodiment, the nanoparticles are gold nanospheres.

In another embodiment, optionally in combination with one or more features of the various embodiments described above or below, the nanoparticles are nanocubes or nanoprisms wherein their inscribed sphere has a diameter of about 10-15 nm.

The conjugates of the invention comprise a plurality of linkers of formula (II),

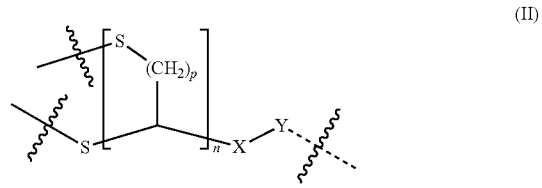

wherein ---, X, Y, n, and p have the meanings as previously described.

In the linker of formula (II), X represents a $(C_2-C_{20})$ hydrocarbon chain, or a $(C_2-C_{20})$hydrocarbon chain wherein at least one carbon atom is replaced by a carbonyl group or a heteroatom selected from the group consisting of O and N; and wherein these $(C_2-C_{20})$hydrocarbon chains are optionally substituted with one or more substituents selected from the group consisting of halogen, OH, $CONH_2$, $CO_2(C_1-C_6)$ alkyl and —CHO.

For the purposes of the present invention, the term $(C_2-C_{20})$hydrocarbon chain relates to a linear or branched hydrocarbon chain comprising from 2 to 20 carbon atoms which may optionally comprise one or more unsaturations in the form of double bonds and/or triple bonds.

In the linker of formula (II), n represents 0 or 1. When n is 0, the linker is attached to the metallic nanoparticle NP through the only available sulfur atom; whereas when n is 1, it is attached to the nanoparticle NP through the two sulfur atoms as illustrated below:

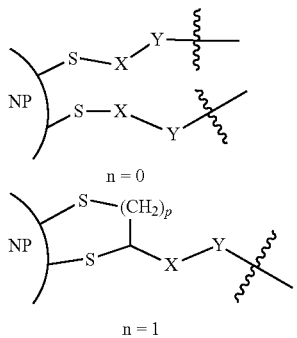

In one embodiment, optionally in combination with one or more features of the various embodiments described above or below, in the linker of formula (II), n=0.

In another embodiment, optionally in combination with one or more features of the various embodiments described above or below, in the linker of formula (II), n=1.

In one embodiment, optionally in combination with one or more features of the various embodiments described above or below, in the linker of formula (II), X represents a saturated $(C_6-C_{15})$hydrocarbon chain or a $(C_6-C_{15})$hydrocarbon chain wherein at least one carbon atom is replaced by a carbonyl group or a heteroatom selected from the group consisting of O and N, optionally substituted as previously defined.

In another embodiment, optionally in combination with one or more features of the various embodiments described above or below, in the linker of formula (II), X represents an unsubstituted $(C_2-C_{20})$hydrocarbon chain or a $(C_2-C_{20})$hydrocarbon chain wherein at least one carbon atom is replaced by a carbonyl group or a heteroatom selected from the group consisting of O and N, particularly an unsubstituted $(C_2-C_{20})$hydrocarbon chain.

In another embodiment, optionally in combination with one or more features of the various embodiments described above or below, in the linker of formula (II), X represents —$(CH_2)_m$— and, wherein m represents a value from 2 to 20, more particularly from 6 to 15, even more particularly from 8 to 12, and even more particularly m is 10 or 11.

In one embodiment, optionally in combination with one or more features of the various embodiments described above or below, an amount equal to or higher than 55% of the total amount of linkers present in the nanoparticle are linkers of formula (II).

In another embodiment, optionally in combination with one or more features of the various embodiments described above or below, an amount from 50 to 100%, more particularly from 55 to 95%, more particularly from 60 to 95% and even more particularly from 75 to 95% of the total amount of linkers present in the nanoparticle are linkers of formula (II).

In one embodiment, optionally in combination with one or more features of the various embodiments described above or below, all the linkers L of the conjugates of the invention are linkers of formula (II), i.e., 100% of the total amount of linkers present in the nanoparticle are linkers of formula (II).

In one embodiment, optionally in combination with one or more features of the various embodiments described above or below, the conjugate of the invention has different types of linkers of formula (II), i.e. linkers of formula (II) having different chemical structures.

In another embodiment, optionally in combination with one or more features of the various embodiments described above or below, all the linkers of formula (II) in the conjugate of the invention are the same, i.e. all the linkers of formula (II) have the same chemical structure.

As mentioned above, in the linker of formula (II), Y may be a sulfonyl moiety or a phosphonyl moiety. In one embodiment, optionally in combination with one or more features of the various embodiments described above or below, in all the linkers of formula (II) present in the conjugate of the invention, Y is a sulfonyl moiety. In another embodiment, optionally in combination with one or more features of the various embodiments described above or below, in all the linkers of formula (II) present in the conjugate of the invention, Y is a phosphonyl moiety. In another embodiment, optionally in combination with one or more features of the various embodiments described above or below, the linkers of formula (II) present in the conjugate of the invention comprise linkers where Y is a sulfonyl moiety and linkers where Y is a phosphonyl moiety. For example, the linkers of formula (II) in the conjugate may comprise 5%, 10%, 20%, 30%, 40%, 50%, 60%, 70%, 80%, or 90% of linkers where Y is a sulfonyl moiety, being the remaining linkers of formula (II) linkers where Y is a phosphonyl moiety.

In another embodiment, optionally in combination with one or more features of the various embodiments described above or below, the linkers of formula (II) are selected from the group consisting of:
- a plurality of linkers wherein n=0, X is —$(CH_2)_m$—, m=10, and Y is a sulfonyl moiety (i.e. 10-mercaptodecanesulfonyl, also referred herein to as MSA linker);
- a plurality of linkers wherein n=0, X is —$(CH_2)_m$—, m=11, and Y is a sulfonyl moiety (i.e. 11-mercaptoundecylsulfonyl);
- a plurality of linkers wherein n=0, X is —$(CH_2)_m$—, m=10, and Y is a phosphonyl moiety (10-mercaptodecylphosphonyl);
- a plurality of linkers wherein n=0, X is —$(CH_2)_m$—, m=11, and Y is a phosphonyl moiety (11-mercaptoundecylphosphonyl, also referred herein to as MPA); and
- a combination thereof.

In one embodiment of the first aspect, optionally in combination with one or more features of the various embodiments described above or below, the linkers L of the conjugates of the invention comprise a plurality of formula (II), and a plurality of linkers of formula (III):

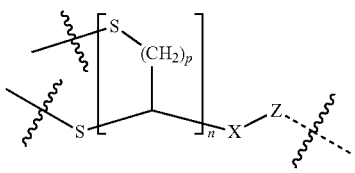

(III)

wherein X, p, and n are as defined for the linkers of formula (II), and

---- is either absent or alternatively represents a single bond; wherein:

when ---- is absent, Z is a moiety of formula (iii):

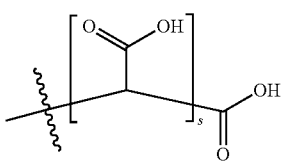

(iii)

wherein s represents a value from 0 to 1; and when ---- is a single bond, Z is a moiety of formula (iii'), which is attached to A by the oxygen atoms:

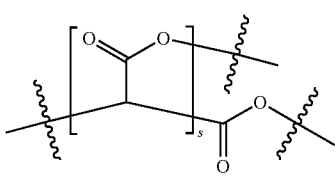

(iii')

wherein s represents a value from 0 to 1.

The linkers of formula (III) are attached to the nanoparticle, and, when they are not in ionic form, are also attached to groups A. These groups A are platinum (II) biradicals independently selected from the group consisting of formula (IV), formula (V), formula (VI), and a pharmaceutically acceptable salt of any of them as previously defined; wherein when the platinum (II) biradical is attached to a linker of formula (III), and s=1, it is attached to one molecule of linker of formula (III); and when s=0; the platinum (II) biradical is attached to two independent linker molecules of formula (III).

In one embodiment of the third aspect, the nanoparticle further comprises linkers of formula (III) which are attached to the nanoparticle, and groups A attached to the linkers of formula (III); with the condition that an amount equal to or higher than 50% of the linkers of formula (II) and formula (III) of the conjugate are in ionic form when the conjugate is in an aqueous medium; and wherein the linkers of formula (II), the linkers of formula (III), and the groups A are as previously defined.

This embodiment may alternatively be formulated as the conjugate of the third aspect, wherein the nanoparticle further comprises linkers of formula (III) which are attached to the nanoparticle, and wherein an amount equal to or lower than 50% of the linkers of formula (II) and (III) are attached to groups A; wherein the linkers of formula (II), the linkers of formula (III), and the groups A are as previously defined.

In one embodiment, optionally in combination with one or more features of the various embodiments described above or below, from 55 to 95%, even more particularly from 75 to 95%, of the linkers L are linkers of formula (II), and from 5 to 45%, even more particularly from 5 to 25%, of the linkers L are linkers of formula (III).

Like in the linkers of formula (II), when in the linkers of formula (III), n is 0, the linker is attached to the metallic nanoparticle NP through the only available sulfur atom; whereas when n is 1, it is attached to the nanoparticle NP through the two sulfur atoms.

In one embodiment, optionally in combination with one or more features of the various embodiments described above or below, in the linker of formula (III), n=0.

In another embodiment, optionally in combination with one or more features of the various embodiments described above or below, in the linker of formula (III), n=1.

In one embodiment, optionally in combination with one or more features of the various embodiments described above or below, in the linker of formula (III), s=0.

In another embodiment, optionally in combination with one or more features of the various embodiments described above or below, in the linker of formula (III), s=1.

In one embodiment, optionally in combination with one or more features of the various embodiments described above or below, in the linker of formula (III), X represents a saturated $(C_6-C_{15})$hydrocarbon chain or a $(C_6-C_{15})$hydrocarbon chain wherein at least one carbon atom is replaced by a carbonyl group or a heteroatom selected from the group consisting of O and N, optionally substituted as previously defined.

In another embodiment, optionally in combination with one or more features of the various embodiments described above or below, in the linker of formula (III), X represents an unsubstituted $(C_2-C_{20})$hydrocarbon chain or a $(C_2-C_{20})$ hydrocarbon chain wherein at least one carbon atom is replaced by a carbonyl group or a heteroatom selected from the group consisting of O and N, particularly an unsubstituted $(C_2-C_{20})$hydrocarbon chain.

In another embodiment, optionally in combination with one or more features of the various embodiments described above or below, in the linker of formula (III), X represents —$(CH_2)_m$— and, wherein m represents a value from 2 to 20, more particularly from 6 to 15, even more particularly from 8 to 12, and even more particularly m is 10 or 11.

In one embodiment, optionally in combination with one or more features of the various embodiments described above or below, the linkers of formula (III) are selected from the group consisting of:

a plurality of linkers wherein n=0, X is —$(CH_2)_m$—, m=10, and s=0, (i.e. 11-mercaptoundecanoyl, also referred herein to as MUA);

a plurality of linkers wherein n=1, p=2, X is —$(CH_2)_m$—, m=4, and s=0; and a combination thereof.

In another embodiment, optionally in combination with one or more features of the various embodiments described above or below, the conjugates of the invention comprise a plurality of linkers of formula (II) selected from:

linkers of formula (II) wherein n=0, X is —$(CH_2)_m$—, m=10, and Y is a sulfonyl moiety;

linkers of formula (II) wherein n=0, X is —$(CH_2)_m$—, m=11, and Y is a sulfonyl moiety;

a plurality of linkers wherein n=0, X is —$(CH_2)_m$—, m=10, and Y is a phosphonyl moiety;

linkers of formula (II), wherein n=0, X is —(CH$_2$)$_m$—, m=11, and Y is a phosphonyl moiety; and
a combination thereof; and
optionally a plurality of linkers of formula (III) selected from:
linkers of formula (III), wherein n=0, X is —(CH$_2$)$_m$—, m=10, and s=0;
linkers of formula (III), wherein n=1, p=2, X is —(CH$_2$)$_m$—, m=4, and s=0;
a combination thereof.

As mentioned above, part of the linkers of the conjugate (e.g. only linkers of formula (II) or a mixture of linkers of formula (II) and linkers of formula (III)) are attached to A groups which are platinum (II) biradicals independently selected from the group consisting of formula (IV), formula (V), formula (VI):

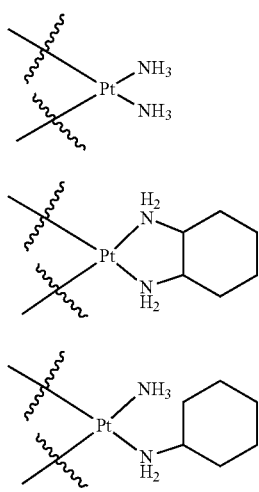

The remaining linkers of the conjugate, in particular, an amount equal to or higher than 50% of the linkers, are deprotonated, i.e. in anionic form when the conjugates are in an aqueous medium.

This means that when the conjugates of the invention comprise a number of linkers, particularly lower than 45% of the total amount of linkers, which have a structure other than formula (II), such as linkers of formula (III), then the amount equal to or higher than 50% of the linkers that have to be in anionic form refers to the total amount of the linkers of the conjugate, including the linkers of formula (II) and the linkers having a structure other than formula (II), such as linkers of formula (III).

In one embodiment, optionally in combination with one or more features of the various embodiments described above or below, from 50 to 90%, from 50 to 80%, from 55 to 75%, from 60 to 70%, and more particularly about 65% of the linkers present in the conjugate, with respect to the total amount of linkers, are in ionic form when the conjugates are in an aqueous medium under neutral or basic conditions.

In another embodiment, optionally in combination with one or more features of the various embodiments described above or below, from 10 to 49%, from 20 to 49%, from 25 to 45%, from 30 to 40%, and more particularly about 35% of the linkers present in the conjugate, with respect to the total amount of linkers, are attached to groups A.

The total number of linkers on the nanoparticles can be estimated by considering the footprint of the thiol molecules used as linkers on gold (0.21 nm$^2$). For example, there could be at most 2930 molecules of thiol molecules onto a 14 nm nanoparticle according to this calculation. The loading of Pt is measured by inductively coupled plasma mass spectrometry (ICP-MS). The number of Pt per nanoparticle can be then calculated knowing the concentration of nanoparticles. In a typical synthesis, a 14 nm nanoparticle is loaded with around 500 molecules of Pt compound. Assuming that every Pt compound binds to two terminal groups of a linker of formula (II), which would be an occupation of 35% of the ligands in the example, leaving 65% in its ionic form when the conjugates are in an aqueous medium.

Even if they are not specifically mentioned, any stereoisomers of the platinum biradicals of formulas (IV), (V) and (VI) are contemplated herein and form part of the invention. Besides, the platinum biradicals may be in salt form.

There is no limitation on the type of salt of the compounds of the invention that can be used, provided that these are pharmaceutically acceptable when they are used for therapeutic purposes. The term "pharmaceutically acceptable salts" embraces salts commonly used such as, without limitation, chloride, nitrate or hydroxide.

The preparation of pharmaceutically acceptable salts can be carried out by methods known in the art. For instance, they can be prepared by conventional chemical methods. The platinum compounds and their salts may differ in some physical properties but they are equivalent for the purposes of the present invention.

Generally, the partial functionalization of the conjugates as defined above with platinum compounds gives rise to a surface disorder. Packing of the molecules of platinum containing drug to the nanoparticle, especially by their reactive ends, protects the molecules from biodegradation until they are released.

Thus, the conjugates of the invention are stable in the sense that they do not precipitate in a medium as it has been mentioned above, and in the sense that the platinum containing drug does not substantially detach from the nanoparticle in the working environment. In the context of the invention, the expression "does not substantially detach from the nanoparticle" means that at least 70%, more particularly 80%, 85%, 90% or 95% of the platinum containing drug does not substantially detach from the nanoparticle in 24 h. In an aqueous medium, at least 90% of the platinum containing drug of the conjugates of the invention does not substantially detach from the nanoparticle in 24 h.

The platinum (II) biradicals as defined above are attached to two linker molecules of formula (II) wherein ---- is a single bond, and Y is either a sulfonyl moiety of formula (i'), or alternatively a phosphonyl moiety of formula (ii'), through the oxygen atom of the moiety of formula (i') or (ii') thereby forming 0-Pt bonds with each of these, as illustrated below:

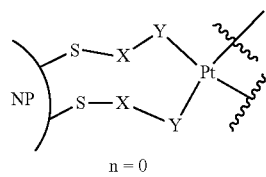

n = 0

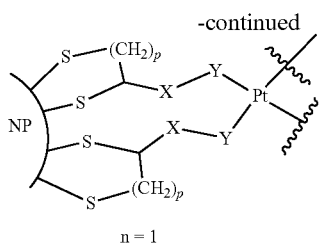

When the conjugates further comprise linkers of formula (III) and these are attached to platinum (II) compounds, the platinum (II) biradical may be attached to the linkers of formula (III) through one or two molecules of linker. Thus, when in the linker of formula (III), s=1, the platinum (II) biradical is attached to one molecule of linker of formula (III), thereby forming two COO—Pt bonds with the same linker molecule; and when s=0; the platinum (II) biradical is attached to two independent linker molecules of formula (III), thereby forming a COO—Pt bond with each of these two linker molecules as illustrated below:

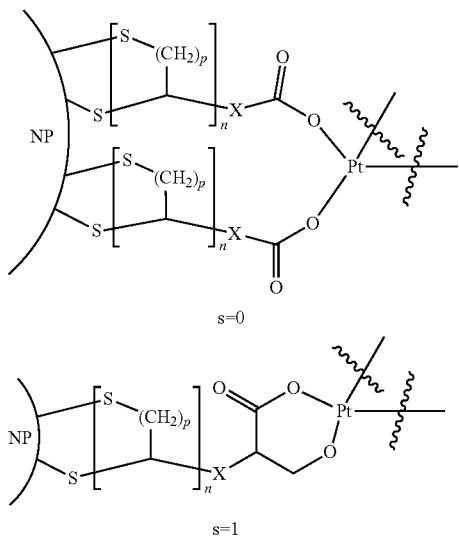

In one embodiment, optionally in combination with one or more features of the various embodiments described above or below, the platinum biradical shows cis configuration.

In one embodiment, optionally in combination with one or more features of the various embodiments described above or below, the platinum biradical has the formula (IV).

The conjugates of the invention have colloidal stability in a medium. The term "colloidal stability" as used herein means that the conjugates of the invention, when dispersed in a medium, are able to resist aggregation (i.e. precipitation). A dispersion that has colloidal stability in a medium exhibits a long shelf-life and has the appearance of a solution. The colloidal stability of the conjugates of the invention is essential since if the conjugates are not stable, they do not show any benefit either in vivo or in vitro in respect to the free drug. UV-Vis spectroscopy is a useful technique to determine the colloidal stability of conjugates. In case of irreversible aggregation leading to precipitation, a red shift and broadening of the surface plasma resonance (SPR) peak with respect to the corresponding peak observed for the corresponding unfunctionalized nanoparticles is observed. More particularly, the red shift in case of aggregation is equal to or higher than 15 nm, more particularly equal to or higher than 25 nm, with respect to the peak observed for the corresponding unfunctionalized nanoparticles (i.e. nanoparticles without linkers).

In one embodiment, optionally in combination with one or more features of the various embodiments described above or below, the conjugates of the invention show colloidal stability in physiologic conditions, that is, the condition or state of the body or bodily functions comprising pH close to neutral (i.e. pH about 7) and high saline concentration.

As it will be described in detail below, in the preparation of a conjugate having colloidal stability it is key to control the number of the platinum compound molecules which are attached to the linker molecules, so that a sufficient amount of the latter remain deprotonated in vivo. Thus, the concentration of platinum compound that a conjugate can support is related to the surface charge. At the working pH the linker molecules are deprotonated and therefore charged. Generally, the working pH corresponds to the pH under physiological conditions. The addition of the platinum coordination complex quenches part of that charge. This can be measured by the decrease in the zeta-potential values at a given pH. It is well known that a colloidal particle generally needs about 30 mV (positive or negative) to be stable against aggregation. This value is dependent on pH and ionic strength.

In one embodiment, optionally in combination with one or more features of the various embodiments described above or below, the conjugates of the invention have a surface electrostatic absolute charge (zeta-potential) equal to or higher than 25 mV, more particularly equal to or higher than 30 mV, under physiological conditions.

As mentioned above, the conjugates of the invention (which using a simplified nomenclature may be referred to as NP-L-A), may be conveniently prepared by a two-step process, firstly by preparing an intermediate conjugate comprising a nanoparticle NP and a plurality of linkers L (using a simplified nomenclature, the intermediate conjugate of the invention is also referred to as NP-L), wherein the linkers are attached to the nanoparticle NP through the available sulfur atoms (step a); and secondly, attaching the platinum (II) containing compound to this intermediate conjugate (step b). To monitor the conjugation, X-Ray Photoelectron Spectroscopy (XPS) may be used.

In the first step of the process, an excess of a compound of formula (IIa) or formula (IIb),

 (IIa)

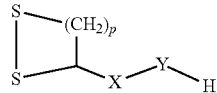
 (IIb)

or a stereoisomer or a salt of any of these compounds as defined above, is reacted with a gold, silver or platinum nanoparticle NP in an aqueous solution, to give rise to the intermediate conjugate of formula NP-L as defined above, wherein:
when a compound of formula (IIa) or a salt thereof is used, an intermediate conjugate is obtained wherein in the linker of formula (II), n is 0; and when a compound of formula (IIb) or a salt thereof is used, an intermediate conjugate is obtained wherein in the linker of formula (II), n is 1.

This first step is shown in the following scheme:

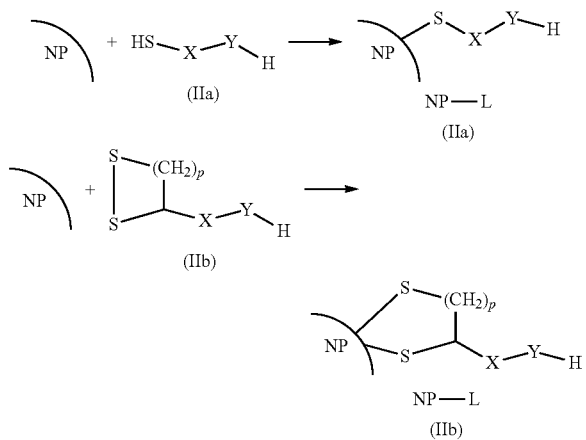

The uncoated metallic nanoparticles used as starting material may be prepared by using synthesis protocols for nanoparticles that allow the simple and scalable production of monodisperse nanoparticles with control of size and shape. In particular, the nanoparticles may be prepared by rapid injection of a metallic salt selected from a salt of Au, Ag and Pt in a reducing agent, thus producing a temporally discrete homogeneous nucleation employed for the production of monodisperse metallic nanoparticles. The reducing agent may be, for example, citrate at high temperature (classical Turkevitch method), sodium borohydride or a mixture of sodium borohydride and ascorbic acid, optionally in the presence of Cetyl Trimethyl Ammonium Bromide (CTAB). For example, the nanoparticles may be prepared as described in Langmuir 2011 27 (17), 11098-11105.

The formation of metallic nanoparticles may be observed by a change in colour in the reaction medium. Depending on the method used the nanoparticles obtained will have a different size and shape in the presence of the right surfactants as CTAB.

In one embodiment, optionally in combination with one or more features of the various embodiments described above or below, step a) is carried out with an excess from 2 to 500, more particularly from 20 to 70 equivalents, of the compound of formula (IIa) or formula (IIb) with respect to the calculated amount necessary to coat the entire nanoparticle. Typically, this reaction is carried out at room temperature.

Generally, it is assumed that this reaction in the presence of an excess of a compound of formula (IIa) or formula (IIb), or a stereoisomer or a salt of any of these formulas, leads to an intermediate conjugate NP-L, wherein the whole surface is coated with moieties L. As mentioned above only one type of linkers of formula (II) or different types of linkers may be used. Additionally, further linkers such as the linkers of formula (III) as previously defined may also be combined with the linkers of formula (II). Linkers of formula (III) may be introduced in the conjugates as described in WO 2010/069941.

Using a simplified nomenclature, when the compound of formula (IIa) is 10-mercapto-decanesulfonic acid or 11-mercaptoundecylphosphonic acid, the intermediates obtained are herein also referred to as NP-MSA and NP-MPA, respectively.

In one embodiment, optionally in combination with one or more features of the various embodiments described above or below, step a) is carried out in the presence of a base. In a particular embodiment, the base is NaOH.

Small nanoparticles are difficult to purify by centrifugation, therefore the non-reacted molecules of the compound of formula (IIa) or formula (IIb) may be eliminated via dialysis of the colloidal solution present in solution after conjugation, together with the remaining reducing agent used in the synthesis of the nanoparticles, if needed.

Thus, in one embodiment, optionally in combination with one or more features of the various embodiments described above or below, in step a) after NP-L is formed, the non-reacted molecules of the compound of formula (IIa) or formula (IIb), and optionally the remaining reducing agent used in the synthesis of the nanoparticles, are eliminated from the reaction of the colloidal solution, more particularly by dialysis.

In the second step of the process (step b), the intermediate conjugates of formula NP-L are further reacted with a platinum compound selected from the group consisting of formula (IVa), formula (Va) and formula (VIa), including the stereoisomers or salts of all of them,

(IVa)

(Va)

(VIa)

to give rise to a conjugate of as previously defined, wherein A is a platinum (II) biradical selected from the group consisting of formula (IV), formula (V) and formula (VI) respectively, wherein the biradical of formulas (IV), (V) and (VI) is optionally in form of a salt. This reaction may be carried out in an aqueous solution in the presence of a base (e.g. at pH 8.3) in order to deprotonate the sulfonic of phosphonic acid groups of the linker of formula (IIa) or formula (IIb).

The compounds (IVa), (Va) and (VIa), including the stereoisomers of all of them, may form a salt in the presence of an anion such as, for example, chloride or nitrate.

As mentioned above, in order to obtain a soluble conjugate of the invention, that is a conjugate having colloidal stability in the medium, some charge has to be maintained at the surface to provide the NPs with enough electrostatic charge and repulsion to avoid aggregation and precipitation. Thus, the surface is coated with linker molecules ending in sulfonyl or phosphonyl groups, which at physiological pH are deprotonated and present negative surface charge. Then, platinum drug molecules are linked to a fraction of the sulfonyl or phosphonyl terminations, so that some of the surface charge is cancelled, but leave enough charge for the electrostatic repulsion.

In order to reach the desired degree of drug loading (i.e. the highest possible therapeutic effects while preserving enough surface charge to avoid destabilization and aggregation) two different approaches can be followed: a) a previously calculated amount of platinum compound, which complies with the above requirements, is mixed with the NP-L intermediate conjugates, or alternatively b) an excess of platinum compound is mixed with the NP-L intermediate conjugates, and the reaction is stopped when the condition that an amount equal to or higher than 50% of the linkers L of the conjugate are in ionic form when the conjugate is in an aqueous medium is met.

The expression "excess of platinum compound" that is mixed with the NP-L intermediate conjugates as used herein refers to an excess with respect to the theoretical amount needed for fulfilling the above-mentioned condition.

In the first case a), the amount of the platinum (II) compound has to be previously calculated. This amount may be determined by routine tasks. In particular, a calibration curve using different amounts of platinum (II) compound may be used. The idea behind this is that different amounts of platinum (II) compounds are reacted with the intermediate conjugates and the resulting conjugates are analysed by UV-Vis spectroscopy. When the amount of platinum compound is too high to lead to a conjugate having colloidal stability, and thus, an aggregate is formed, this can be detected by the red-shift of the UV-Vis peak when comparing the UV-Vis spectra of the resulting conjugate and the corresponding intermediate conjugate. Thus, the amount of platinum compound is subsequently reduced until no aggregation is observed.

In the second case b), when an excess of platinum compound is used, the conjugation is stopped before too many platinum compound molecules are attached to the linker molecules. The inventors have found that, when monitoring the attachment of the platinum compound to linker coated nanoparticles, if the process is not efficiently stopped, the platinum compound continues coating the linker layer and the nanoparticles become unstable.

Therefore, when working with an excess of platinum compound, the attachment of platinum compound molecules to the linker molecules has to be stopped when the charge of platinum drug is maximal and the resulting conjugate is still stable. This cannot be achieved spontaneously. To stop the conjugation the conjugating solution is placed for example in a dialysis bag where from the free platinum compound molecules escape rapidly leaving the conjugate NP-L partially coated with the platinum compound. The time at which the reaction has to be stopped can be previously calculated. This last procedure has the advantage that it is faster and more controlled.

Conjugation may be monitored by the combination of series of experiments including dynamic light scattering (DLS), UV-Vis spectroscopy, Zeta Potential, transmission electron microscopy (TEM), optical microscopy, Gel Electrophoresis and ICP-MS for quantitative analysis.

In one embodiment, optionally in combination with one or more features of the various embodiments described above or below, step b) comprises reacting the intermediate conjugate obtained in step a) with the platinum (II) compound as previously defined in a calculated amount such that in the final conjugate an amount equal to or higher than 50% of the linkers L are in ionic form when the conjugate is in an aqueous medium.

In another embodiment, optionally in combination with one or more features of the various embodiments described above or below, step b) comprises reacting the intermediate conjugate obtained in step a) with an excess of the platinum (II) compound as previously defined and stopping the reaction when in the final conjugate an amount equal to or higher than 50% of the linkers L are in ionic form when the conjugate is in an aqueous medium.

In one more particular embodiment, the reaction is stopped by eliminating the non-reacted platinum (II) compound of the solution, e.g. via dialysis.

In one embodiment, optionally in combination with one or more features of the various embodiments described above or below, step b) is carried out with an excess from 1 to 10 times, more particularly from 1.2 to 5 times, of the platinum (II) compound as previously defined with respect to the theoretical amount needed for fulfilling with the condition that an amount equal to or higher than 50% of the linkers L of the conjugate are in ionic form when the conjugate is in an aqueous medium.

In one embodiment, optionally in combination with one or more features of the various embodiments described above or below, step b) is carried out at basic pH, more particularly at a pH from 8.2 to 8.5, even more particularly at pH=8.3.

The compound of formula (IVa) may be synthesized starting from the compound of formula (VII) (cisplatin) or formula (VIII) (carboplatin); the compound of formula (Va) may be synthesized starting from the compound of formula (IX) (oxaliplatin); and the compound of formula (VIa) may be synthesized starting from the compound of formula (X).

(VII)

(VIII)

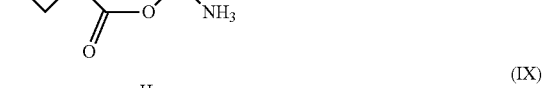

(IX)

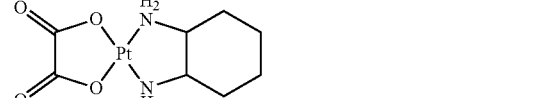

(X)

In the case of cisplatin, the conversion is carried out by treating the compound with a source of a Ag cation, such as $AgNO_3$, to remove Cl from the cisplatin molecule (VII) and yield the hydrated species (IVa). Similarly, a compound of formula (X) may be converted into a compound of formula (VIa) by analog methods.

In the case of carboplatin (VIII), the compound is converted to a compound of formula (IVa) by hydrolysis of the COO bonds by standard methods well-known in the art. Similarly, a compound of formula (IX) may be converted into a compound of formula (IVa) by analog methods.

Alternatively, the compounds of formula (Va) and (VIa) may be obtained by a two-step synthesis comprising: 1) reacting PtCl₄ with the corresponding amine: cyclohexane-1,2-diamine or ammoniac/cyclohexylamine to yield intermediates (Vb) and (VIb), and

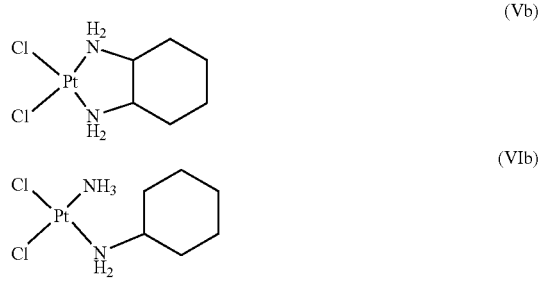

2) treating the intermediates obtained in step 1) with a source of a Ag cation, such as AgNO₃, to remove Cl and yield the hydrated species (Va) and (VIa) respectively.

The undesired side-products, in particular, trans platinum compounds, may be removed by means of chromatography.

The fact that a platinum compound of formula (IVa), (Va) or (VIa) is conjugated to the intermediate conjugate NP-L instead of the platinum compounds of formulas (VII) to (X) has important consequences. Thus, in the conjugates of the invention, coordination bonds between the linker and the platinum compound are formed. These bonds, as already mentioned are strong and provide for stability of the molecule, in particular in a medium at physiological conditions. These bonds are only hydrolyzed at low pH, such as the one present in the in endosomes and endolysosomes.

Although cisplatin and oxaliplatin derivatives (instead of cisplatin and oxaliplatin themselves, respectively) are used for conjugation, using a simplified nomenclature, the conjugates of the invention containing cisplatin and oxaliplatin derivatives are also referred herein to as NP-L-cisplatin and NP-L-oxaliplatin, respectively.

The present invention also relates to pharmaceutical compositions. These compositions may be formulated in solid or liquid form.

In one embodiment, optionally in combination with one or more features of the various embodiments described above or below, the administration of the pharmaceutical composition is intramuscular, intravenous, intraperitoneal or intratumoral. Generally, suitable formulations include aqueous and non-aqueous, isotonic sterile injection solutions which have suitable pH and stability, which can contain for instance anti-oxidant agents, buffers and bacteriostatic agents; and aqueous and non-aqueous sterile suspensions that may include suspending agents, solubilizers, thickening agents, stabilizers, biocompatible polymers, polysaccharides and preservatives.

As already mentioned the conjugates of the invention may be useful for the treatment of cancer in a patient suffering therefrom, especially in cases where surgery is not feasible.

Representative cancers of interest include, but are not limited to head, neck and lung tissue; gastrointestinal tract and pancreas, such as gastric carcinoma, colorectal adenoma, colorectal carcinoma and pancreatic carcinoma; hepatic tissue, such as hepatocellular carcinoma; Kidney and urinary tract, such as bladder carcinoma, renal carcinoma; breast tissue, such as breast carcinoma; neural tissue, such as neuroblastoma and meningioma malignant; skin tissue, such as melanoma; and hematological tissues, such as lymphoma and leukemia.

Those of skill in the art will readily appreciate that dose levels may vary, among others, as a function of the specific compound, the nature of the delivery vehicle, and the nature of the tumor to be treated. In a particular embodiment, in order to have realistic doses for the in vivo application of the invention, the concentration of the conjugates is increased about 50 times. To this end, the nanoparticles are precipitated by centrifugation and the pellet recovered and re-dissolved in progressively decreasing amounts of solvent without losing any stability. Alternatively, tangential flow filtration may be also used.

The conjugates of the invention have the advantage that they reduce the side effects in comparison with the currently used therapies with cisplatin and analogs.

The conjugates of the invention may concentrate on the tumors as a result of the Enhanced Permeability and Retention effect (EPR). Briefly, the EPR effect, is the result of defective tissue integrity, changes in permeation mediators and impaired lymphatic drainage in tumors. Thus, the vascular endothelium of tumors tends to have relatively large gaps that allow larger molecular species up to 200 nm to permeate the tissue rather than in healthy tissues. The altered permeation mediators and impaired lymphatic drainage mechanism then assure that the molecules that have penetrated the tumor stay there. Thus, the conjugates of the invention passively accumulate in the tumor and from there are internalized via endocytosis.

Moreover, due to the conjugation, the conjugates are inactive in the systemic circulation and they are only activable after reaching tumour, or in the liver, as particulate matter does, where no toxicity has been observed. When entering the tumoral cell, once in the endosome, the low pH used by the digestive apparatus of the cell (the endolysosome, resulting from the fusion of the endosome and the lysosome) leads to the hydrolysis of the coordination bond between the linker and the platinum drug, so that the platinum drug is released close to the nucleous.

As already mentioned, the invention also relates to a method for the treatment of cancer comprising administering to a mammal in need thereof, including a human, a therapeutically effective amount of a conjugate as previously defined together with one or more pharmaceutically acceptable excipients. In a particular embodiment, the later method further comprises locally irradiating the tumor at any frequency (from gamma to XR, NIR and MW) in order that the platinum drug becomes more effective. In all the cases, gold core interacts with radiation ultimately producing heat or other effects that can cause damage to tumor tissue. Particularly, gold core produces Auger electrons after interacting with X-rays, which is finally translated into high local doses of free radicals, inducing double strand damage to DNA.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

1. Synthesis of Conjugates
Characterization Techniques
   1) UV-Vis Spectroscopy: UV-Visible spectra were acquired with a Shimadzu UV-2400 spectrophotometer. 1 mL of nanoparticles or conjugates were placed in a cell, and spectral analysis was performed in the 300 nm to 800 nm range.
   2) Transmission electronic microscopy (TEM): Gold nanoparticles were visualized using 80 keV TEM (JEOL 1010). Ten microliter droplets of the sample were drop casted onto a piece of ultrathin Formvar-coated 200-mesh copper grid (Ted-pella, Inc.) and left to dry in air.
   3) Inductively coupled plasma mass spectrometry (ICP-MS): The amount of Pt on the nanoparticles was determined by ICP-MS analysis of the sample after digestion with aqua regia.

Example 1: Synthesis of Gold Nanospheres (AuNP) Functionalized with MPA and a Derivative from Cisplatin (AuNPs-MPA-Cisplatin)

1.1. Synthesis of Gold Nanoparticles (AuNP, Diameter of 14 nm)

Figure 2:
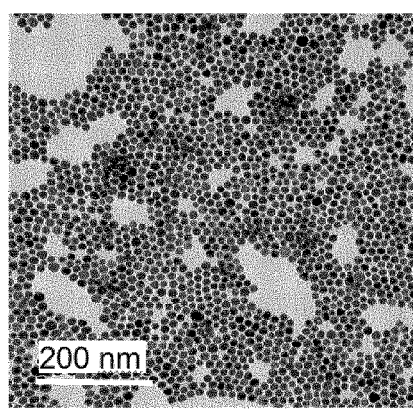
FIG. 2 is a representative TEM image of the nanoparticles obtained in example 1 (left) and the corresponding histogram (C=counts, right) showing an average diameter for the nanoparticle of 14.6+/−1.8 nm.
Figure 2:
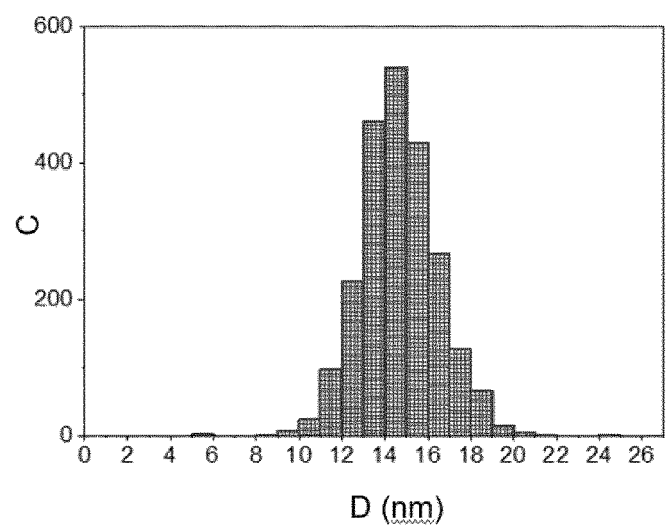

A sodium citrate solution in water (2.2 mM, 150 mL) was heated to reflux in a 250 mL three-neck round-bottom flask with a heating mantle. After 10 minutes, $HAuCl_4 \cdot 3H_2O$ aqueous solution (25 mM, 1 mL) was quickly added. The solution was left for 5 minutes under vigorous stirring. Color changed fast to bluish gray and then to pink and finally to red. Then, the gold nanoparticles solution was left to cool down to 90° C. 1 mL $HAuCl_4 \cdot 3H_2O$ aqueous solution (25 mM) was added and the solution was kept under vigorous stirring for 10 minutes at 90° C. This addition of gold at 90° C. was repeated 2 more times. Solution was transferred to a glass bottle and left at room temperature. Characterization of the synthesis of the obtained gold nanoparticles: FIG. 2 (left) is a representative TEM image of the nanoparticles and FIG. 2 (right) shows the corresponding histogram, average diameter was 14.6+/−1.8 nm.

1.2. Functionalization with MPA (AuNP-MPA)

A basic aqueous solution of 11-mercaptoundecylphosphonic acid (MPA) was freshly prepared before addition to 150 mL AuNPs: 17.7 mg MPA+6.6 mL MilliQ water+54 μL NaOH 2M were mixed and sonicated until total dissolution (Final MPA concentration=10 mM). The obtained MPA solution (6.6 mL, 10 mM) was mixed with 150 mL of 13 nm AuNPs as synthesized above under vigorous stirring during the first 5 minutes and soft stirring overnight. Volumes were calculated for 150 mL, but they can be scaled up proportionally. The resulting nanoparticles were concentrated by centrifugation. 1 mL aliquots of AuNP-MPA solution was placed in 1.5 mL eppendorf tubes. They were centrifuged at 14000 rcf for 18 minutes. Supernatants were discarded and the pellets collected together. Final volume was adjusted with water to be 50-fold lower than the initial volume. Nanoparticles were then transferred to regenerated cellulose 20 KDa dialysis membranes and dialyzed twice against 2 L water+160 μL 2M NaOH.

1.3. Functionalization with $[Pt(H_2O)_2(NH_2)_2](NO_3)_2$ (AuNP-MPA-cisPt)

AuNP-MPA solution (as obtained above) was firstly adjusted to pH=8.3 by adding small volumes of 0.2 M NaOH. Then, 78 μL of $[Pt(H_2O)_2(NH_3)_2](NO_3)_2$ aqueous solution (4.3 mg/mL) was added dropwise to 3 mL concentrated AuNP-MPA under vortexing. The solution was left under agitation for 30 minutes and then transferred to regenerated cellulose 20 KDa dialysis membranes and dialyzed twice against 2 L water+160 μL 2M NaOH.

Figure 3:
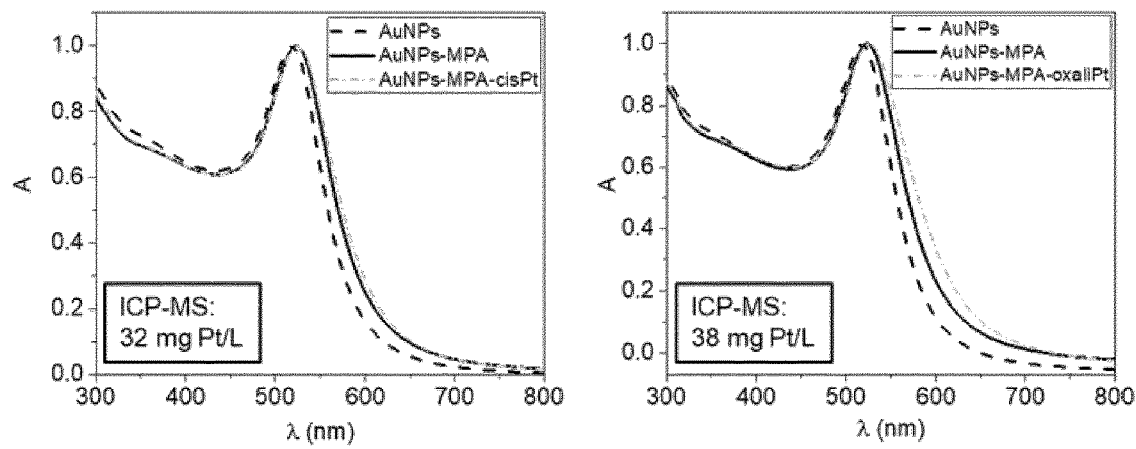
FIG. 3 shows the UV-Vis spectra of the different stages of functionalization of example 1 (AuNP, AuNP-MPA, and AuNP-MPA-cisPt, left) and of example 2 (AuNP, AuNP-MPA, and AuNP-MPA-oxaliPt, right).

Characterization of the conjugated of example 1: FIG. 3 (left) shows the UV-Vis spectra of the different stages of functionalization (AuNP, AuNP-MPA, and AuNP-MPA-cisPt). The loading of platinum compound was >30 mg Pt/L.

Example 2: Synthesis of Gold Nanospheres Functionalized with MPA (AuNP-MPA) and a Derivative from Oxaliplatin (AuNPs-MPA-oxaliPt)

Following the same procedure as described in example 1 but using a derivative from oxaliplatin instead of a derivative from cisplatin, the desired nanoparticles were obtained. In particular, 234 μL of $[[Pt(H_2O)_2(1R,2R\text{-diaminocyclohexane})]$ (2.1 mg/mL) aqueous solution was added dropwise to 3 mL concentrated AuNP-MPA as prepared in example 1 under vortexing.

Characterization of Example 2: FIG. 3 (right) shows the UV-Vis spectra of the different stages of functionalization (AuNP, AuNP-MPA, and AuNP-MPA-oxaliPt). The loading of platinum compound was >30 mg Pt/L.

Example 3: Synthesis of Gold Nanospheres Functionalized with MSA (AuNP-MSA) and a Derivative from Cisplatin (AuNPs-MSA-cisPt)

Following the same procedure as described in example 1 but using 10-mercaptodecane-sulfonic acid (MSA) instead of MPA, the desired nanoparticles were obtained. In particular, 150 mL of 13 nm AuNPs as synthesized above were added to a MSA solution (32.5 mL, 10 mM) under vigorous stirring during the first 5 minutes and soft stirring overnight. 78 μL of $[Pt(H_2O)_2(NH_3)_2](NO_3)_2$ aqueous solution (4.3 mg/mL) was added dropwise to 3 mL concentrated AuNP-MSA under vortexing.

Figure 4:
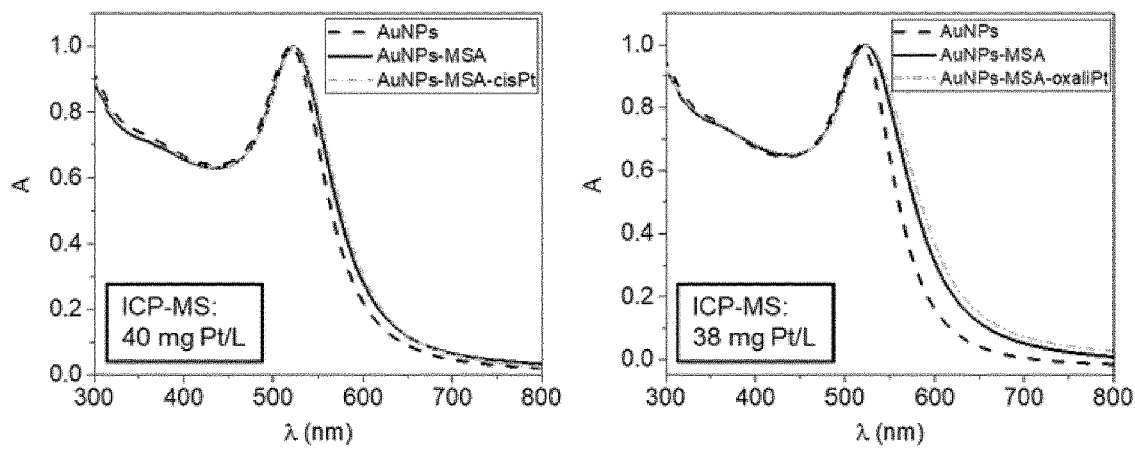
FIG. 4 shows the UV-Vis spectra of the different stages of functionalization of example 3 (AuNP, AuNP-MSA, and AuNP-MSA-cisPt, left) and of example 4 (AuNP, AuNP-MSA, and AuNP-MSA-oxaliPt, right).

Characterization of Example 3: FIG. 4 (left) shows the UV-Vis spectra of the different stages of functionalization (AuNP, AuNP-MSA, and AuNP-MSA-cisPt). The loading of platinum compound was >30 mg Pt/L.

Example 4: Synthesis of Gold Nanospheres Functionalized with MSA (AuNP-MSA) and a Derivative from Oxaliplatin (AuNPs-MSA-oxaliPt)

Following the same procedure as described in example 3 but using a derivative from oxaliplatin instead of a derivative from cisplatin, the desired nanoparticles were obtained. In particular, 234 μL of $[[Pt(H_2O)_2(1R,2R\text{-diaminocyclohexane})]$ (2.1 mg/mL) aqueous solution was added dropwise to 3 mL concentrated AuNP-MPA as prepared in example 1 under vortexing.

Characterization of Example 4: FIG. 4 (right) shows the UV-Vis spectra of the different stages of functionalization (AuNPs, AuNPs-MSA, AuNPs-MSA-oxaliPt). The loading of platinum compound was >30 mg Pt/L.

Comparative Example 1: Synthesis of Gold Nanospheres Functionalized with MUA (AuNP-MUA) and a Derivative from Cisplatin (AuNPs-MUA-Cisplatin)

Following the same procedure as described in example 1 but using but using 11-mercaptoundecanoic acid (MUA) instead of MPA, the desired nanoparticles were obtained.

Figure 5:
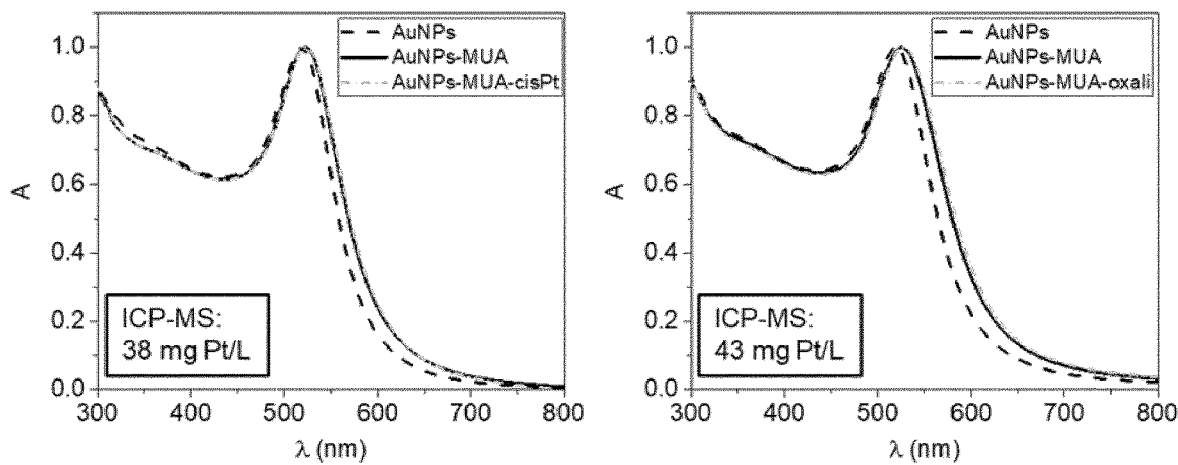
FIG. 5 shows the UV-Vis spectra of the different stages of functionalization of comparative example 1 (AuNP, AuNP-MUA, and AuNP-MUA-cisPt, left) and of comparative example 2 (AuNP, AuNP-MUA, and AuNP-MUA-oxaliPt, right) and the loading of cisplatin.

Characterization of comparative example 1: FIG. 5 (left) shows the UV-Vis spectra of the different stages of functionalization (AuNPs, AuNPs-MUA, AuNPs-MUA-cisPt). The loading of platinum compound is shown in the inset.

Comparative Example 2: Synthesis of Gold
Nanospheres Functionalized with MUA
(AuNP-MUA) and a Derivative from Oxaliplatin
(AuNPs-MUA-Oxaliplatin)

Following the same procedure as described in example 2 but using but using MUA instead of MPA.

Characterization of comparative example 2: FIG. 5 (right) shows the UV-Vis spectra of the different stages of functionalization (AuNPs, AuNPs-MUA, AuNPs-MUA-oxaliPt). The loading of platinum compound is shown in the inset.

2. Release of Pt from the Conjugates
Preparation of Buffers 50 mL of the following buffers were prepared in 50 mL PS tubes:
  1a. pH 7.6: 50 mM HEPES (4-(2-hydroxyethyl)-1-piperazineethanesulfonic acid)+11 mg/mL BSA (Bovine Serum Albumin)
  1b. pH 6.2: 50 mM MES (2-(N-morpholino)ethanesulfonic acid)+11 mg/mL BSA
  1c. pH 4.4: 50 mM Gly/HCl+11 mg/mL BSA
  1d. pH 2.8: 50 mM Gly/HCl+11 mg/mL BSA
  pH was readjusted after adding BSA with 2M NaOH or HCl Sample Preparation and Collection 4.5 mL of 1.x buffer+0.5 mL of the conjugates of examples 1-4 and comparative examples 1-2. Samples were incubated at room temperature and softly stirred. 0.5 mL aliquots of each sample were taken at 0 h, 24 h, 48 h, 72 h and 96 h. After collection, samples were immediately centrifuged (15000 rcf, 30 min). The resulting supernatants were collected and another 2 centrifugation cycles were performed to ensure that supernatant was transparent (i.e. no absorbance at 520 nm), which indicated the absence of AuNPs.

Quantification of Released Pt

The amount of Pt in the resultant supernatants was analyzed by ICP-MS—The initial loading of Pt in the tested conjugates was analyzed by ICP-MS by directly measuring the amount of Pt after digestion of gold nanoparticles with aqua regia. A control (conjugates in water) was added to assess/discard any unspecific release of Pt derivative and to quantify any possible not bounded Pt derivative present in the initial solution of nanoparticles. 4.5 mL of water+0.5 mL of tested conjugates was mixed and treated as indicated above for the rest of the samples. The amount of Pt in the resulting supernatant was also analyzed by ICP-MS.

Figure 6:
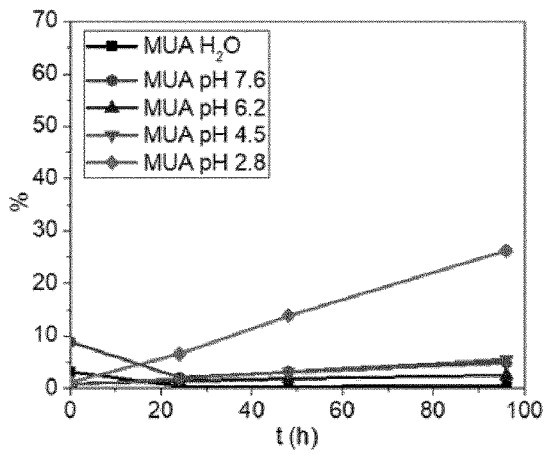
FIG. 6 shows the % of platinum compound released from the conjugate of comparative example 1 (AuNP-MUA-cisPt, left) and the conjugate of comparative example 2 (AuNP-MUA-oxaliPt, right) at different pH values.
Figure 6:
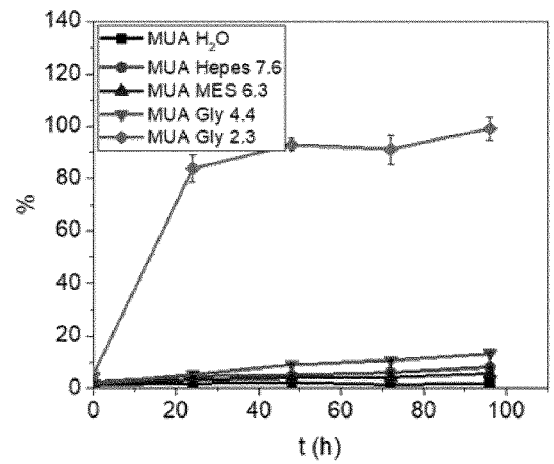
Figure 7:
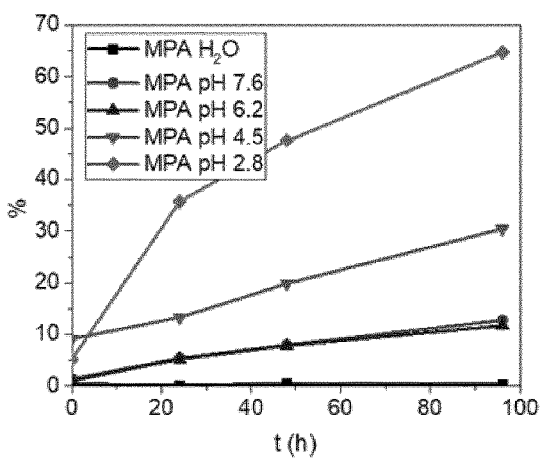
FIG. 7 shows the % of platinum compound released from the conjugate of example 1 of the invention (AuNP-MPA-cisPt, left) and the conjugate of example 2 of the invention (AuNP-MPA-oxaliPt, right) at different pH values.
Figure 7:
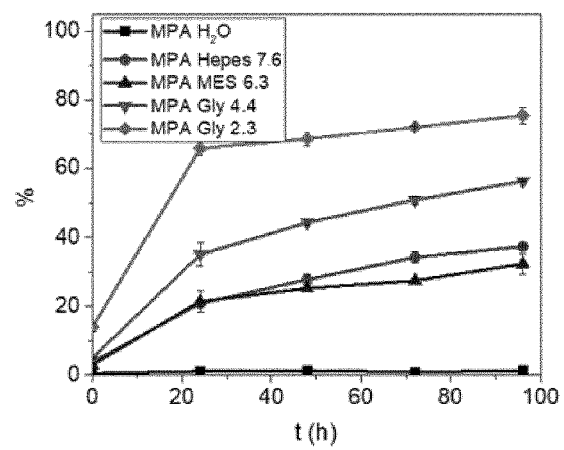
Figure 8:
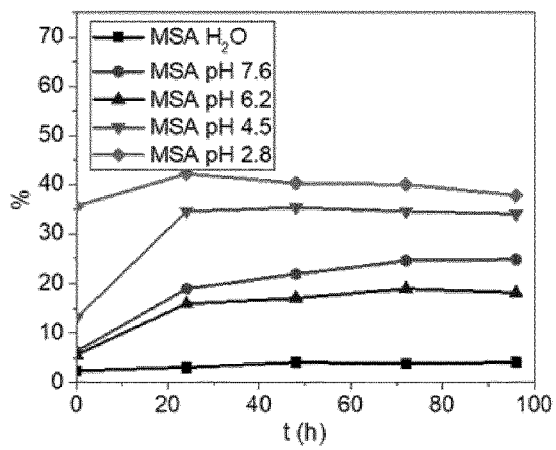
FIG. 8 shows the % of platinum compound released from the conjugate of example 1 of the invention (AuNP-MSA-cisPt, left) and the conjugate of example 2 of the invention (AuNP-MSA-oxaliPt, right) at different pH values.
Figure 8:
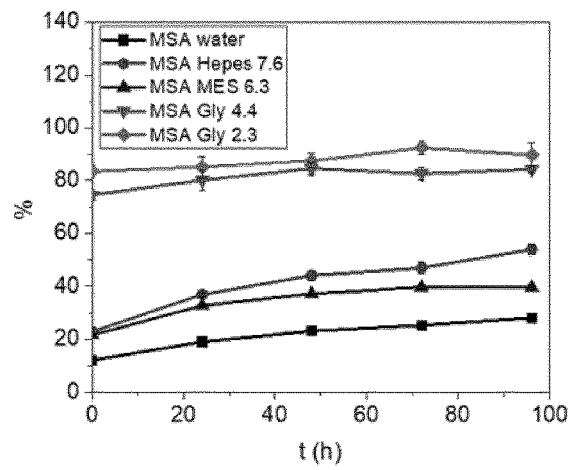

The results are shown in FIG. 6-8. It was seen that the link between AuNP-MPA or AuNP-MSA and Pt derivatives was more labile than the link between AuNP-MUA and Pt derivatives. This was translated to a higher release of the Pt derivative at low pH for MPA and MSA compared to MUA.

3. Stability of the Conjugates

In Water: The different conjugates were left as synthesized. 5 µL of each sample was mixed with 995 µL of water in a plastic cuvette at the different time points of the experiment (0 h, 1 day, 3 days, 6 days, 9 days, 14 days). UV-Vis spectra was then measured from 300 to 800 nm.

In Cell culture media: 120 µL of a 5.2 mM BSA solution in water was added to 1 mL of every conjugate and softly agitated. 4 mL of cell culture media (Dulbecco's modification of Eagle medium (DMEM) supplemented with 10% Fetal Bovine Serum (FBS)) was added to 1 ml of the conjugate+BSA solution. Aliquots were taken at 0 and 24 hours. 100 µL of each sample was mixed with 900 µl of water in a plastic cuvette. UV-Vis spectra was then measured from 300 to 800 nm.

Figure 9:
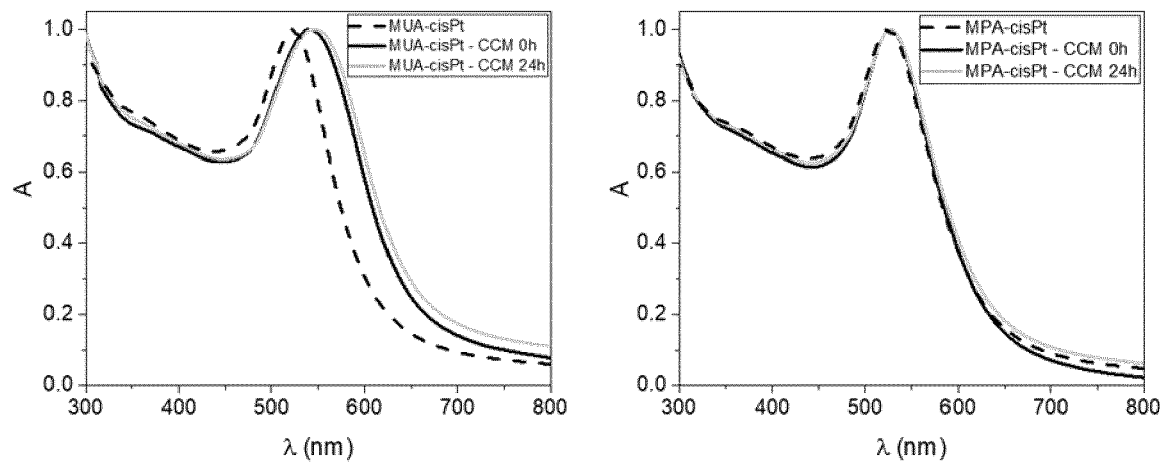
FIG. 9 shows the results for the stability in cell culture media of the conjugates of comparative example 1 (left) and the conjugates of example 1 (right) until 24 h.

It was observed that conjugates of examples 1-4 showed maintenance of colloidal stability at all the time points measured here. FIG. 9 shows the results for the stability in cell culture media of the conjugates of comparative example 1 (left) and example 1 (right) respectively until 24 h. In fact, the stability was monitored up to 96 h, but no differences were seen. In the case of MUA, although colloidal stability was maintained a slight broadening of their UV-Vis spectrum band in cell culture medium was observed. This was indicative of a slight degree of clustering. A different scenario was observed for MPA-functionalized conjugates, where no differences in the spectra after incubation in cell culture media were observed.

4. Cell Viability

Cell viability experiments were performed. In this case, mouse urothelial carcinoma cells (MB49) were treated with the conjugates of example 1 (AuNPs-MPA-cisplatin) or the intermediate conjugate AuNP-MPA, the conjugates of example 3 (AuNPs-MSA-cisplatin) or the intermediate conjugate AuNP-MSA and compared to cells treated with the conjugates of comparative example 1 (AuNPs-MUA-cisplatin) or the corresponding intermediate conjugate AuNP-MUA. The treatment consisted on 24 hours incubation with the different nanoparticles followed by 24 hours incubation with fresh media. Cell viability was measured using a commercial assay (PrestoBlue™) and following instructions provided by the manufacturer.

Figure 10:
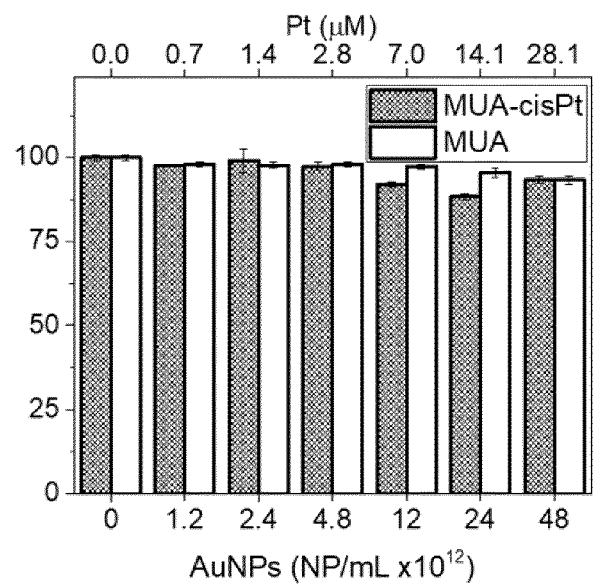
FIG. 10 shows the results of cell viability experiments with the conjugates of comparative example 1 (AuNPs-MUA-cisplatin).
Figure 11:
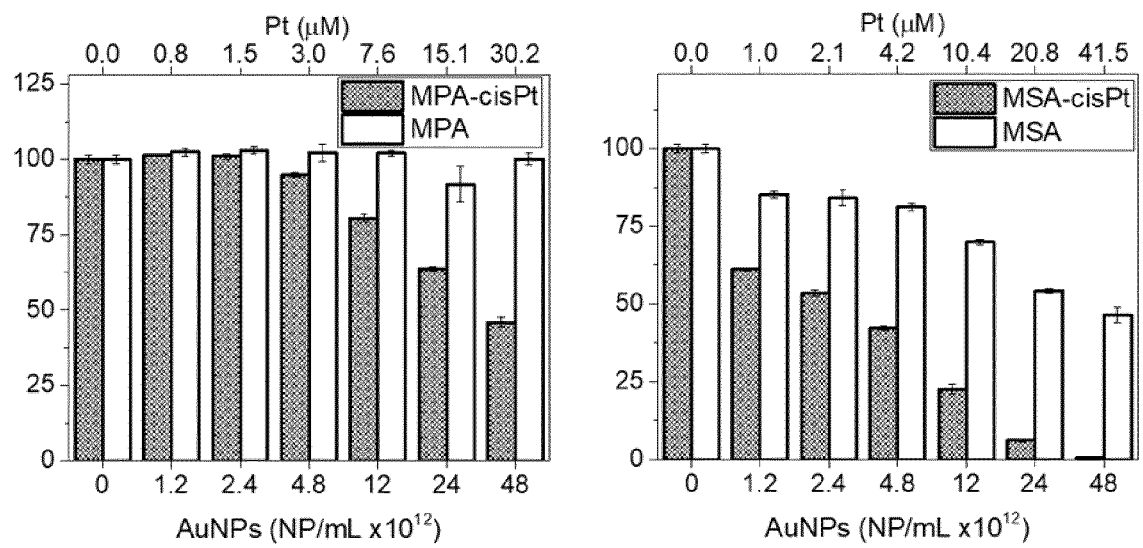
FIG. 11 shows the results of cell viability experiments with the conjugates of example 1 (AuNPs-MPA-cisplatin) (left) and example 3 (AuNPs-MSA-cisplatin) (right).

Results are shown in FIGS. 10 and 11. It was observed that the conjugates of example 1 (AuNPs-MPA-cisplatin) (FIG. 11 (left)) and example 3 (AuNPs-MSA-cisplatin) (FIG. 11 (right)) showed a significant decrease in cell viability with concentrations of $12\times10^{12}$ AuNPs/mL or higher for AuNPs-MPA-cisplatin and $1.2\times\times10^{12}$ AuNPs/mL or higher for AuNPs-MPA-cisplatin. On the other hand, no decrease in cell viability was observed for the conjugates of comparative example 1 (AuNPs-MUA-cisplatin) (FIG. 10). In all cases, a control of same nanoparticles without cisplatin showed no toxicity (MUA and MPA) or a much lower toxicity at the highest concentrations (MSA), which indicated that the observed decrease in viability was mainly due to cisplatin. Note that cisplatin has to be released from the nanoparticle to cause damage to DNA.

CITATION LIST

WO 2010/069941

Bastús N. G. et al, "Kinetically Controlled Seeded Growth Synthesis of Citrate-Stabilized Gold Nanoparticles of up to 200 nm: Size Focusing versus Ostwald Ripening", Langmuir 2011 27 (17), 11098-11105.

The invention claimed is:

1. A conjugate having colloidal stability in a medium wherein the conjugate comprises a nanoparticle NP, a plurality of linkers of formula (II) attached to the nanoparticle,

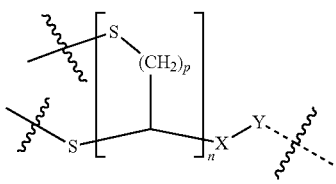
(II)

and a plurality of groups A attached to the linkers, wherein:

NP is a gold, silver or platinum nanoparticle;

n represents 0 or 1; wherein:
when n is 0, the linker of formula (II) is attached to the nanoparticle NP through the sulfur atom; and when n is 1, the linker of formula (II) is attached to the nanoparticle NP through the two sulfur atoms;

p represents a value selected from 1 to 3; and

X represents a $(C_2-C_{20})$ hydrocarbon chain, or a $(C_2-C_{20})$ hydrocarbon chain wherein at least one carbon atom is replaced by a carbonyl group or a heteroatom selected from the group consisting of O and N; and wherein these $(C_2-C_{20})$ hydrocarbon chains are optionally substituted with one or more substituents selected from the group consisting of halogen, OH, $CONH_2$, $CO_2$ $(C_1-C_6)$alkyl and —CHO;

---- is either absent or alternatively represents a single bond; wherein:
when ---- is absent, Y is either a sulfonyl moiety of formula (i), or alternatively a phosphonyl moiety of formula (ii):

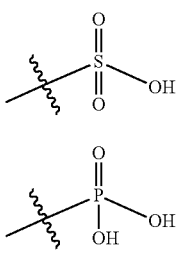
(i)
(ii)

and when ---- is a single bond, Y is either a sulfonyl moiety of formula (i'), or alternatively a phosphonyl moiety of formula (ii'), which is attached to A by the oxygen atom:

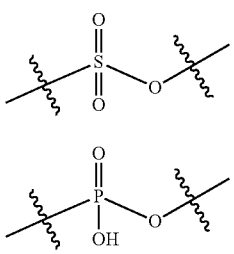
(i')
(ii')

the groups A are platinum (II) biradicals independently selected from the group consisting of formula (IV), formula (V), formula (VI), and a pharmaceutically acceptable salt of any of them:

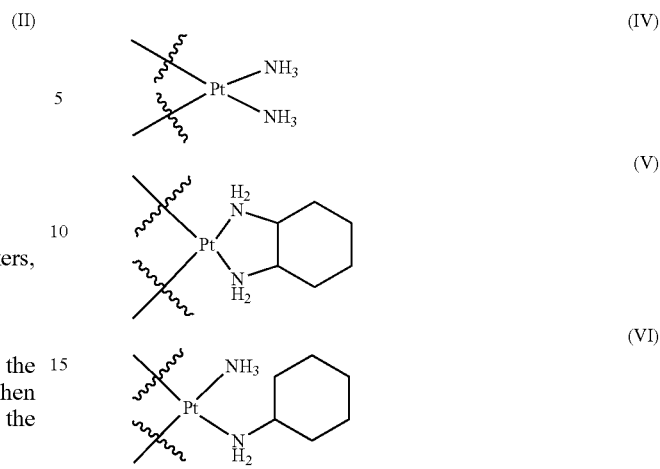
(IV)
(V)
(VI)

wherein the platinum (II) biradical is attached to two independent linker molecules of formula (II) wherein ---- is a single bond, and Y is either a sulfonyl moiety of formula (i'), or alternatively a phosphonyl moiety of formula (ii'), through the oxygen atom of the moiety of formula (i') or (ii');

with the condition that an amount equal to or higher than 50% of the linkers of formula (II) are in ionic form when the conjugate is in an aqueous medium.

2. The conjugate according to claim 1, wherein in the linker of formula (II) Y comprises a sulfonyl moiety.

3. The conjugate according to claim 1, wherein in the linker of formula (II) Y comprises a phosphonyl moiety.

4. The conjugate according to claim 1, wherein in the linker of formula (II) n is 0.

5. The conjugate according to claim 1, wherein in the linker of formula (II) X represents —$(CH_2)_m$—, wherein m represents a value selected from 6 to 15.

6. The conjugate according to claim 1, wherein the linkers of formula (II) are selected from the group consisting of:
a plurality of linkers wherein n=0, X is —$(CH_2)_m$—, m=10, and Y is a sulfonyl moiety;
a plurality of linkers wherein n=0, X is —$(CH_2)_m$—, m=11, and Y is a sulfonyl moiety;
a plurality of linkers wherein n=0, X is —$(CH_2)_m$—, m=10, and Y is a phosphonyl moiety;
a plurality of linkers wherein n=0, X is —$(CH_2)_m$—, m=11, and Y is a phosphonyl moiety; and
a combination thereof.

7. The conjugate according to claim 1, wherein the nanoparticle further comprises linkers of formula (III) which are attached to the nanoparticle,

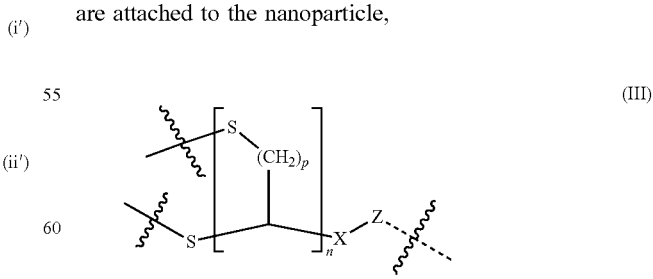
(III)

and groups A attached to the linkers of formula (III), wherein:
wherein X, p, and n are as defined for the linkers of formula (II) in claim 1, and ---- is either absent or alternatively represents a single bond; wherein:

when ---- is absent, Z is a moiety of formula (iii):

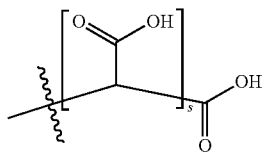
(iii)

wherein s represents a value selected from 0 to 1; and
when ---- is a single bond, Z is a moiety of formula (iii'), which is attached to A by the oxygen atoms:

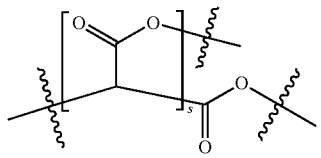
(iii')

wherein s represents a value selected from 0 to 1;
the groups A are platinum (II) biradicals independently selected from the group consisting of formula (IV), formula (V), formula (VI), and a pharmaceutically acceptable salt of any of them:

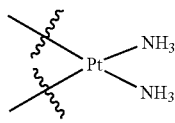
(IV)

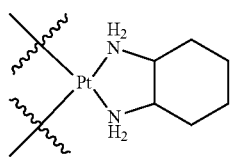
(V)

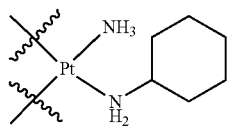
(VI)

wherein when the platinum (II) biradical is attached to a linker of formula (III), and s=1, it is attached to one molecule of linker of formula (III); and when s=0; the platinum (II) biradical is attached to two independent linker molecules of formula (III); and
with the condition that an amount equal to or higher than 50% of the linkers of formula (II) and formula (III) of the conjugate are in ionic form when the conjugate is in an aqueous medium.

8. The conjugate according to claim 1, wherein the nanoparticle is a gold nanoparticle.

9. The conjugate according to claim 1, wherein the nanoparticle is a nanosphere having a diameter selected from 4 to 20 nm.

10. The conjugate according to claim 1, which has colloidal stability in a physiological medium.

11. The conjugate according to claim 1, wherein A is a platinum (II) biradical of formula (IV).

12. A process for the preparation of a conjugate as defined in claim 1, comprising the following steps:
a) reacting a gold, silver or platinum nanoparticle NP with an excess of a compound selected from the group consisting of formula (IIa), formula (IIb), and a salt either of the compound of formula (IIa) or of the compound of formula (IIb),

(IIa)

(IIb)

wherein X, and p have the same meaning as defined in claim 1, and Y is a sulfonyl moiety of formula (i') or a phosphonyl moiety of formula (ii') as defined in claim 1; in an aqueous solution to give rise to an intermediate conjugate; wherein:
when a compound of formula (IIa) or a salt thereof is used, an intermediate conjugate is obtained wherein in the linker of formula (II), n is 0; and
when a compound of formula (IIb) or a salt thereof is used, an intermediate conjugate is obtained wherein in the linker of formula (II), n is 1;
b) reacting the intermediate conjugate obtained in step a) with an appropriate amount of a platinum (II) compound selected from the group consisting of formula (IVa), formula (Va), formula (VIa), and a salt of any of the formulas (IVa), (Va) and (VIa):

(IVa)

(Va)

(VIa)

in an aqueous solution in the presence of a base, to obtain the desired conjugate.

13. A pharmaceutical composition comprising a conjugate as defined in claim 1, together with one or more pharmaceutically acceptable excipients or carriers.

14. A method for the treatment of cancer in a mammal, the method comprising administering to said mammal an effective amount of the conjugate of as defined in claim 1, together with one or more pharmaceutically acceptable excipients.

15. A method for the treatment of cancer in a mammal, the method comprising administering to said mammal the pharmaceutical composition as defined in claim 13, wherein the composition is administered by intravenous, subcutaneous or intramuscular injection.

16. The conjugate according to claim 2, wherein in the linker of formula (II) n is 0.

17. The conjugate according to claim 3, wherein in the linker of formula (II) n is 0.

18. The conjugate according to claim 2, wherein in the linker of formula (II) X represents $-(CH_2)_m-$, wherein m represents a value selected from 6 to 15.

19. The conjugate according to claim 3, wherein in the linker of formula (II) X represents $-(CH_2)_m-$, wherein m represents a value selected from 6 to 15.

* * * * *